US011835516B2

(12) United States Patent
Wada et al.

(10) Patent No.: US 11,835,516 B2
(45) Date of Patent: Dec. 5, 2023

(54) DETERMINATION METHOD AND KIT FOR DETERMINING POSSIBILITY OF REDUCED RENAL FUNCTION

(71) Applicants: National University Corporation Okayama University, Okayama (JP); Glycotechnica Ltd., Kanagawa (JP)

(72) Inventors: Jun Wada, Okayama (JP); Koki Mise, Okayama (JP); Masao Yamada, Kanagawa (JP)

(73) Assignees: National University Corporation Okayama University, Okayama (JP); Glycotechnica Ltd., Kanagawa (JP)

( * ) Notice: Subject to any disclaimer, the term of this patent is extended or adjusted under 35 U.S.C. 154(b) by 970 days.

(21) Appl. No.: 16/498,634

(22) PCT Filed: Mar. 27, 2018

(86) PCT No.: PCT/JP2018/012399
§ 371 (c)(1),
(2) Date: Sep. 27, 2019

(87) PCT Pub. No.: WO2018/181292
PCT Pub. Date: Oct. 4, 2018

(65) Prior Publication Data
US 2021/0109091 A1    Apr. 15, 2021

(30) Foreign Application Priority Data

Mar. 31, 2017    (JP) .................. 2017-072324

(51) Int. Cl.
*G01N 33/53*    (2006.01)
(52) U.S. Cl.
CPC ..... *G01N 33/5308* (2013.01); *G01N 2400/00* (2013.01); *G01N 2800/042* (2013.01); *G01N 2800/044* (2013.01); *G01N 2800/347* (2013.01)
(58) Field of Classification Search
CPC ....... G01N 2800/044; G01N 2800/347; G01N 2400/00
IPC ................................. G01N 33/5308
See application file for complete search history.

(56) References Cited

U.S. PATENT DOCUMENTS

| 6,150,115 A | 11/2000 | Miyaura et al. |
| 2007/0202535 A1 | 8/2007 | Hirabayashi et al. |

FOREIGN PATENT DOCUMENTS

| JP | 10-332690 A | 12/1998 |
| JP | 2008-216137 A | 9/2008 |
| JP | 2010-256132 A | 11/2010 |
| WO | 2005064333 A1 | 7/2005 |

OTHER PUBLICATIONS

Fufaa, Gudeta et al., "Association of urinary KIM-1, L-FABP, NAG and NGAL with incident end-stage renal disease and mortality in American Indians with type 2 diabetes mellitus", Diabetologia, 58: 188-198 (2015).
Niewczas, Monika A. et al., "Circulating TNF Receptors 1 and 2 Predict ESRD in Type 2 Diabetes", J. Am. Soc. Nephrol., 23: 507-515 (2012).
Nowak, Natalia et al., "Increased plasma kidney injury molecule-1 suggests early progressive renal decline in non-proteinuric patients with type 1 diabetes", Kidney International, 89: 459-467 (2016).
Mise, Koki et al., "Identification of Prognostic Factors through Glycan Profiling for Type 2 Diabetes", Abstract of paper presented at the 60th Annual Meeting of the Japanese Society of Nephrology on Mar. 13, 2017.
Mise, Hiroki et al., "Identification of prognostic/predictive factor for kidney by sugar chain profiling in type 2 diabetic patients", The Japanese Journal of Renology, 59(3): 228 (2017).
International Search Report and Written Opinion, dated Jul. 3, 2018, issued in corresponding International Application No. PCT/JP2018/012399.

*Primary Examiner* — Gyan Chandra
(74) *Attorney, Agent, or Firm* — Kathleen D. Rigaut; Howson & Howson LLP (57) ABSTRACT

Provided are a determination method and a kit both for determining the possibility of the occurrence of deterioration of a renal function in the future. A method according to one aspect of the present invention involves a step of determining the level of Galβ1-3GalNAc and/or Siaα2-6Gal/GalNAc in a sample collected from a subject. A kit according to one aspect of the present invention includes a lectin capable of binding to Galβ1-3GalNAc and/or Siaα2-6Gal/GalNAc.

16 Claims, 3 Drawing Sheets

DETERMINATION METHOD AND KIT FOR DETERMINING POSSIBILITY OF REDUCED RENAL FUNCTION

CROSS-REFERENCE TO RELATED APPLICATIONS

This application is a § 371 of International Application No. PCT/JP2018/012399, filed Mar. 27, 2018, which claims priority from Japanese Patent Application No. 2017-072324, filed Mar. 31, 2017. The entire disclosure of each of the aforesaid applications is incorporated by reference in the present application.

TECHNICAL FIELD

The present invention relates to a determination method of determining a possibility of reduced renal function. The present invention also relates to a kit for predicting reduced renal function.

BACKGROUND ART

Dialysis treatment is the primary treatment method for patients with reduced renal function. However, dialysis treatment must normally be performed about three times per week, which is burdensome for a patient and also causes increased medical costs. According to a "facilities survey" conducted by the Japanese Society for Dialysis Therapy, as of the end of 2015, about 325,000 people are receiving dialysis treatment in Japan (Japanese Society for Dialysis Therapy, *An Overview of Regular Dialysis Treatment in Japan As of Dec. 31, 2015*, 2016, Japanese Society for Dialysis Therapy, p. 2). According to a "patient survey" conducted by the JSDT, about 44% of patients receiving dialysis treatment are patients with diabetic nephropathy (ibid., p. 9).

Currently, useful biomarkers for estimating renal prognosis at an early stage prior to nephropathic progression are desired. As such biomarkers for predicting renal prognosis (whether renal function will be reduced in the future) and vital prognosis (whether a patient will survive) of a patient with a renal disease (for example, a diabetes patient), for example, biomarkers related to inflammation such as TNF-α receptor 1 and TNF-α receptor 2 (see non-patent literature 1) and biomarkers related to tubulointerstitial damage such as NGAL (neutrophil gelatinase-associated lipocalin), L-FABP (L-fatty acid binding protein), and KIM-1 (kidney injury molecule-1) are known (see non-patent literatures 2, 3).

Now, the present inventors subjected samples derived from subjects to an interaction measurement with lectins to measure quantities of sugar chains having affinity with these lectins. As a result, they found that progression of diabetic nephropathy can be detected from the measured sugar-chain quantities (patent literature 1).

CITATION LIST

Patent Literature

Patent literature 1: JP 2010-256132 A (published Nov. 11, 2010)

Non-Patent Literature

Non-patent literature 1: Niewczas, M. A., et al. (2012). Circulating TNF receptors 1 and 2 predict ESRD in type 2 diabetes. *Journal of the American Society of Nephrology*, 23(3), 507-515.

Non-patent literature 2: Fufaa, G. D., et al. (2015). Association of urinary KIM-1, L-FABP, NAG and NGAL with incident end-stage renal disease and mortality in American Indians with type 2 diabetes mellitus. *Diabetologia*, 58(1), 188-198.

Non-patent literature 3: Nowak, N., et al. (2016). Increased plasma kidney injury molecule-1 suggests early progressive renal decline in non-proteinuric patients with type 1 diabetes. *Kidney International*, 89(2), 459-467.

SUMMARY OF THE INVENTION

Problem to be Solved by the Invention

The biomarkers described in non-patent literatures 1 to 3 are shown to be useful as predictors of prognosis in early diabetic nephropathy. However, they have yet to be utilized in everyday clinical settings, and their usefulness is limited. That is, there is room for improvement in biomarkers such as above that predict renal prognosis and the like.

One aspect of the present invention has as an object to provide a means of predicting renal prognosis (whether renal function will be reduced in the future).

Means for Solving the Problem

To solve the above problem, the present inventors used a lectin assay made by GlycoTechnica to perform an exhaustive analysis of relationships between forty-five types of sugar-chain profiles in samples derived from diabetes patients and renal prognosis. As a result, the following four observations were made:

(1) There is a strong positive correlation between binding signals of a first lectin group (MPA, ACA, ABA, and Jacalin) and reduced renal function in the future.

(2) There is a strong positive correlation between high binding signals of a second lectin group (SSA and SNA) and reduced renal function in the future.

(3) There is a strong negative correlation between a binding signal of a third lectin (GSL_I_B4) and reduced renal function in the future.

(4) There is a strong negative correlation between high binding signals of a fourth lectin group (VVA and EEL) and reduced renal function in the future.

Among the above lectins, the binding signals of MPA, ACA, ABA, and Jacalin were particularly important as predictors of reduced renal function in the future. A specific sugar-chain structure shared by MPA, ACA, ABA, and Jacalin was Galβ1-3GalNAc. As such, the inventors thought that a level of Galβ1-3GalNAc in a sample sampled from a subject could serve as a biomarker for predicting whether renal function would be reduced in the future.

Likewise, a specific sugar-chain structure shared by SSA and SNA was Siaα2-6Gal/GalNAc, a specific sugar-chain structure binding with VVA was α-GalNAc, a specific sugar-chain bond binding with GSL_I_B4 was Galα, and a specific sugar-chain structure binding with EEL was Galα1-3Gal. As such, the inventors thought that levels of the above sugar chains in a sample sampled from a subject could serve as biomarkers for predicting whether renal function would be reduced in the future.

The present invention was completed according to the new findings above made by the present inventors. That is, the present invention includes the following configurations:

(1) A determination method of determining a possibility of reduced renal function, including the step of determining a level of Galβ1-3GalNAc and/or a level of Siaα2-6Gal/GalNAc in a sample sampled from a subject.

(2) The determination method of (1), further including the step of determining a level of at least one type selected from a group consisting of α-GalNAc, Galα, and Galα1-3Gal in the sample sampled from the subject.

(3) The determination method of (1) or (2), wherein the step of determining the level of Galβ1-3GalNAc and/or the level of Siaα2-6Gal/GalNAc includes a step of determining a level of a sugar chain that binds with at least one lectin selected from a group consisting of MPA, ACA, ABA, Jacalin, SSA, and SNA.

(4) The determination method of (2), wherein the step of determining the level of at least one type of sugar chain selected from the group consisting of α-GalNAc, Galα, and Galα1-3Gal includes a step of determining a level of a sugar chain that binds with at least one lectin selected from a group consisting of VVA, GSL_I_B4, and EEL.

(5) A determination method of determining a possibility of reduced renal function, including the step of determining a level of a sugar chain that binds with at least one lectin selected from a group consisting of MPA, ACA, ABA, Jacalin, SSA, SNA, VVA, GSL_I_B4, and EEL in a sample sampled from a subject.

(6) The determination method of any one among (1) to (5), wherein the subject is a subject with one or more types of diseases selected from a group consisting of diabetes, hypertension, dyslipidemia, obesity, and hepatic steatosis.

(7) A kit for predicting reduced renal function, provided with a lectin that binds with Galβ1-3GalNAc and/or Siaα2-6Gal/GalNAc.

(8) The kit of (7), further provided with a lectin that binds with at least one type of sugar chain selected from a group consisting of α-GalNAc, Galα, and Galα1-3Gal.

(9) The kit of (7) or (8), wherein the lectin that binds with Galβ1-3GalNAc and/or Siaα2-6Gal/GalNAc is at least one selected from a group consisting of MPA, ACA, ABA, Jacalin, SSA, and SNA.

(10) The kit of (8), wherein the lectin that binds with at least one type of sugar chain selected from α-GalNAc, Galα, and Galα1-3Gal is at least one selected from a group consisting of VVA, GSL_I_B4, and EEL.

(11) A kit for predicting reduced renal function, provided with at least one or more lectins selected from a group consisting of MPA, ACA, ABA, Jacalin, SSA, SNA, VVA, GSL_I_B4, and EEL.

Note that the invention described in patent literature 1 detects a current progression of diabetic nephropathy in a subject. In contrast, the present invention has a completely different object of predicting reduced renal function in the future. That is, according to the present invention, it is possible to identify, for example, a "subject whose renal function is currently favorable but will be reduced in the future" or a "subject whose renal function is currently unfavorable but will be reduced gradually in the future."

Furthermore, it was hitherto completely unknown that a level of a sugar chain such as Galβ1-3GalNAc in a sample of a subject or a binding signal of a specific lectin could serve as a predictor of reduced renal function in the future, and patent literature 1 neither describes nor suggests this. The present invention is provided with sufficient patentability at least in regard to this point.

Effects of Invention

One aspect of the present invention provides a determination method and a kit for determining a possibility of reduced renal function in the future.

EMBODIMENTS OF INVENTION

One example of an embodiment of the present invention is described in detail below, but the present invention is not limited thereto. In the present specification, unless otherwise noted, in representing numerical ranges, "A to B" signifies "A or greater and B or less."

The technical idea of the present invention is described below. However, the following description is an illustration to aid in the understanding of the present invention and does not limit the scope of the present invention in any way.

{1. Determination Method of Determining Possibility of Reduced Renal Function and Acquisition Method of Data}

A determination method of determining a possibility of reduced renal function of one embodiment of the present invention includes a step of determining a level of Galβ1-3GalNAc and/or a step of determining a level of Siaα2-6Gal/GalNAc in a sample sampled from a subject. Note that to simplify description, hereinbelow, (i) "determination method of determining a possibility of reduced renal function" may be notated as "determination method," (ii) "step of determining a level of Galβ1-3GalNAc" may be notated as "Galβ1-3GalNAc level determination step," and (iii) "step of determining a level of Siaα2-6Gal/GalNAc" may be notated as "Siaα2-6Gal/GalNAc level determination step."

According to the above determination method of one embodiment of the present invention, a possibility of reduced renal function can be determined based on the level of Galβ1-3GalNAc and/or the level of Siaα2-6Gal/GalNAc in the above sample.

Furthermore, in one embodiment of the present invention, the above determination compares the level of Galβ1-3GalNAc and/or the level of Siaα2-6Gal/GalNAc against a reference value. The above reference value can be established as appropriate by a medical method, a statistical method, or the like (more specifically, see the literatures cited in the present specification and the examples described in the present specification).

As the above reference value, a plurality of reference values can be established. For example, different reference values may be used according to a condition (such as sex or age) of the subject. Alternatively, magnitudes of the possibility of reduced renal function and the plurality of reference values may be associated as in a "first reference value whereat the possibility of reduced renal function is higher" and a "second reference value whereat the possibility of reduced renal function is lower." Based on such reference values, the possibility of reduced renal function in the subject can be determined even by a non-physician.

For example, in one embodiment of the present invention, according to the above determination method, when the level of Galβ1-3GalNAc is at or above the reference value, it can be determined that the possibility of reduced renal function is high. In another embodiment, according to the above determination method, the possibility of reduced renal function can be determined to be higher the higher the level of Galβ1-3GalNAc is.

Furthermore, in one embodiment of the present invention, according to the above determination method, when the level of Galβ1-3GalNAc is at or below the reference value, it can be determined that the possibility of reduced renal function is low. In another embodiment, according to the above determination method, the possibility of reduced renal function can be determined to be lower the lower the level of Galβ1-3GalNAc is.

The determination method of one embodiment of the present invention can combine a level of a sugar chain and a factor other than a level of a sugar chain. That is, factors such as age, sex, BMI, mean arterial pressure, HbA1c, estimated glomerular filtration rate (eGFR), and urinary albumin-to-creatine ratio (UACR) and a level of a sugar chain can be combined to be able to more accurately determine the possibility of reduced renal function (for example, see the examples).

Here, an essential characteristic of the determination method of one embodiment of the present invention is acquiring data including a level of a sugar chain such as Galβ1-3GalNAc or Siaα2-6Gal/GalNAc in the sample from the above sample. Therefore, the "determination method of predicting reduced renal function" of one aspect of the present invention can also serve as an "acquisition method of data for predicting reduced renal function." That is, in the present specification, the phrase "determination method of predicting a possibility of reduced renal function" is interchangeable with the phrase "acquisition method of data for predicting reduced renal function."

{1-1. Galβ1-3GalNAc Level Determination Step and Siaα2-6Gal/GalNAc Level Determination Step}

The determination method of one embodiment of the present invention includes the Galβ1-3GalNAc level determination step and/or the Siaα2-6Gal/GalNAc level determination step. Each is described below.

{1-1-1. Galβ1-3GalNAc Level Determination Step}

A measurement target in the Galβ1-3GalNAc level determination step is Galβ1-3GalNAc (also "Core O-glycan"). This substance is a sugar chain that is present in living tissue such as renal tissue by being bound with various substances (for example, proteins and lipids). Galβ1-3GalNAc may also be cut free from the various substances and be present in the sample sampled from the subject.

The present inventors first examined types of sugar chains present in a sample derived from a patient with a renal disease at a specific point in time and afterward tracked progression of the renal disease in this patient. As a result, it was found that patients whose renal disease worsened in the future have a large quantity of Galβ1-3GalNAc in the above sample, which led to the completion of the present invention.

As such, in the determination method of one embodiment of the present invention, it can be said that the Galβ1-3GalNAc level determination step is achieved by measuring a quantity of Galβ1-3GalNAc in the sample derived from the subject. However, a specific aspect of the Galβ1-3GalNAc level determination step is not limited to the above measurement. For example, it can be understood that the Galβ1-3GalNAc level determination step can also be achieved by determining a level of a protein involved in producing Galβ1-3GalNAc in the sample derived from the subject, a level of a protein involved in cutting Galβ1-3GalNAc, or a level of a protein involved in converting Galβ1-3GalNAc.

That is, the determination method of one embodiment of the present invention may be a method including a step of determining a level of a protein involved in producing Galβ1-3GalNAc in the sample sampled from the subject. Moreover, a determination method of another embodiment of the present invention may be a method including a step of determining a level of a protein involved in cutting Galβ1-3GalNAc in the sample sampled from the subject. A determination method of yet another embodiment of the present invention may be a method including a step of determining a level of a protein involved in converting Galβ1-3GalNAc in the sample sampled from the subject. Here, "involved in converting Galβ1-3GalNAc" denotes, for example, cutting a portion of Galβ1-3GalNAc and/or adding another substance to Galβ1-3GalNAc.

As the above protein involved in producing Galβ1-3GalNAc, for example, polypeptide N-acetylgalactosaminyltransferase 1 (GALNT1; alias: GALNAC-T1); polypeptide N-acetylgalactosaminyltransferase 2 (GALNT2; alias: GalNAc-T2); polypeptide N-acetylgalactosaminyltransferase 3 (GALNT3; aliases: GalNAc-T3, HFTC, HHS); core 1 synthase, glycoprotein-N-acetylgalactosamine 3-beta-galactosyltransferase 1 (C1GALT1; aliases: C1GALT, T-synthase); C1GALT1 specific chaperone 1 (C1GALT1C1; aliases: C1GALT2, C38H2-L1, COSMC, HSPC067, MST143, TNPS); and glucosaminyl (N-acetyl) transferase 1, core 2 (GCNT1; aliases: C2GNT, C2GNT-L, C2GNT1, G6NT, NACGT2, NAGCT2) can be mentioned (see table 1).

TABLE 1

| Official gene symbol | Name | Aliases |
| --- | --- | --- |
| GALNT1 | polypeptide N-acetylgalactosaminyl-transferase 1 | GALNAC-T1 |
| GALNT2 | polypeptide N-acetylgalactosaminyl-transferase 2 | GalNAc-T2 |
| GALNT3 | polypeptide N-acetylgalactosaminyl-transferase 3 | GalNAc-T3, HFTC, HHS |
| C1GALT1 | core 1 synthase, glycoprotein-N-acetyl-galactosamine 3-beta-galactosyltransferase 1 | C1GALT, T-synthase |
| C1GALT1C1 | C1GALT1 specific chaperone 1 | C1GALT2, C38H2-L1, COSMC, HSPC067, MST143, TNPS |
| GCNT1 | glucosaminyl (N-acetyl) transferase 1, core 2 | C2GNT, C2GNT-L, C2GNT1, G6NT, NACGT2, NAGCT2 |

As the above protein involved in cutting Galβ1-3GalNAc, for example, alpha-N-acetylgalactosaminidase (NAGA; aliases: D22S674, GALB) can be mentioned (see table 2).

TABLE 2

| Official gene symbol | Name | Aliases |
| --- | --- | --- |
| NAGA | alpha-N-acetylgalactosaminidase | D22S674, GALB |

As the above protein involved in converting Galβ1-3GalNAc, for example, ST3 beta-galactoside alpha-2,3- sialyltransferase 2 (ST3GAL2; aliases: Gal-NAc6S, SIAT4B, ST3GALII, ST3GalA.2), ST3 beta-galactoside alpha-2,3-sialyltransferase 1 (ST3GAL1; aliases: Gal-NAc6S, SIAT4A, SIATFL, ST3GalA, ST3GalA.1, ST3GalIA, ST3GalIA,1, ST3O), ST8 alpha-N-acetyl-neuraminide alpha-2,8-sialyltransferase 5 (ST8SIA5; aliases: SIAT8-E, SIAT8E, ST8SiaV), ST6 N-acetylgalactosaminide alpha-2,6-sialyltransferase 3 (ST6GALNAC3; aliases: PRO7177, SIAT7C, ST6GALNACIII, STY), ST6 N-acetylgalactosaminide alpha-2,6-sialyltransferase 4 (ST6GALNAC4; aliases: IV, SIAT3-C, SIAT3C, SIAT7-D, SIAT7D, ST6GALNACIV, ST6GalNAc), ST3 beta-galactoside alpha-2,3-sialyltransferase 5 (ST3GAL5; aliases: SATI, SIAT9, SIATGM3S, SPDRS, ST3GalV), ST8 alpha-N-acetyl-neuraminide alpha-2,8-sialyltransferase 1 (ST8SIA1; aliases: GD3S, SIAT8, SIAT8-A, SIAT8A, ST8SiaI), ST3 beta-galactoside alpha-2,3-sialyltransferase 4 (ST3GAL4; aliases: CGS23, NANTA3, SAT3, SIAT4, SIAT4C, ST-4, ST3GalA.2, ST3GalIV, STZ,gal-NAc6S), and endo-alpha-N-acetylgalactosaminidase (SAPI-O_CDS0469) can be mentioned (see table 3).

phy, mass spectrometry, ELISA, two-dimensional electrophoresis, a protein array, a bead assay, flow cytometry, Bio-Plex (registered trademark), and the like can be mentioned. Moreover, in another aspect, this signifies positioning some indicator relating to the above sugar chain in a hierarchy. That is, determining the level of the sugar chain does not have to include quantification. As such a level determination method, for example, a method of classifying into "no sugar chain present whatsoever" and "sugar chain present" can be mentioned.

Among these, the level determination method by a lectin assay is preferable from a viewpoint of sample pretreatment being easy. This is particularly preferable when using a urine sample as the sample because steps such as concentrating the urine sample and removing proteins included in large quantities in the sample (such as albumin and IgG) are unnecessary.

When determining the level of Galβ1-3GalNAc by a lectin assay, it is preferable to use lectins having binding activity with Galβ1-3GalNAc. As such lectins, MPA (*Maclura pomifera* agglutinin; Osage orange lectin), ACA (*Ama-*

TABLE 3

| Official gene symbol | Name | Aliases |
| --- | --- | --- |
| ST3GAL1 | ST3 beta-galactoside alpha-2,3-sialyltransferase 1 | Gal-NAc6S, SIAT4A, SIATFL, ST3GalA, ST3GalA.1, ST3GalIA, ST3GalIA,1, ST3O |
| ST3GAL2 | ST3 beta-galactoside alpha-2,3-sialyltransferase 2 | Gal-NAc6S, SIAT4B, ST3GALII, ST3GalA.2 |
| ST3GAL4 | ST3 beta-galactoside alpha-2,3-sialyltransferase 4 | CGS23, NANTA3, SAT3, SIAT4, SIAT4C, ST-4, ST3GalA.2, ST3GalIV, STZ, gal-NAc6S |
| ST3GAL5 | ST3 beta-galactoside alpha-2,3-sialyltransferase 5 | SATI, SIAT9, SIATGM3S, SPDRS, ST3GalV |
| ST6GALNAC3 | ST6 N-acetylgalactosaminide alpha-2,6-sialyltransferase 3 | PRO7177, SIAT7C, ST6GALNACIII, STY |
| ST6GALNAC4 | ST6 N-acetylgalactosamininde alpha-2,6-sialyltransferase 4 | IV, SIAT3-C, SIAT3C, SIAT7-D, SIAT7D, ST6GALNACIV, ST6GalNAc |
| ST8SIA1 | ST8 alpha-N-acetyl-neuraminide alpha-2,8-sialyltransferase 1 | GD3S, SIAT8, SIAT8-A, SIAT8A, ST8SiaI |
| ST8SIA5 | ST8 alpha-N-acetyl-neuraminide alpha-2,8-sialyltransferase 5 | SIAT8-E, SIAT8E, ST8SiaV |
| SAPIO_CDS0469 | Endo-alpha-N-acetylgalactosaminidase | None |

Note that the proteins listed above may have a plurality of names and/or abbreviations. To identify these, databases such as UniProtKB, KEGG, CATH, PubMed, and PDB can be used.

The levels of the above proteins can be, for example, expression levels of mRNA coding the above proteins, expression levels of the above proteins, concentrations of the above mRNA or proteins, or potencies (such as enzyme activities) of the above proteins. These values can be measured by normal methods (such as an immunostaining method).

Note that in one embodiment of the present invention, the Galβ1-3GalNAc level determination step is a step that is performed in vitro.

In the present specification, "determining a level of Galβ1-3GalNAc" can mean that the determination of the level of the above sugar chain includes quantifying a concentration of this sugar chain included in the sample. As such a level determination method, binding-activity measurement using lectins (lectin assay), liquid chromatogra-

*ranthus caudatus* agglutinin; love-lies-bleeding lectin), ABA (*Agarucus bisporus* agglutinin; mushroom lectin), Jacalin (jackfruit lectin), BPL (*Bauhinia purpurea* lectin; purple orchid tree lectin), and PNA (peanut agglutinin) can be mentioned. Note that these lectins are conventionally known lectins and that amino-acid sequence information thereof is available from various databases.

The above Galβ1-3GalNAc level determination step can be a step of using lectins that bind specifically with Galβ1-3GalNAc to determine a level of the sugar chain binding with these lectins. Moreover, the above Galβ1-3GalNAc level determination step can be a step of determining a level of the sugar chain binding with at least one lectin (for example, one lectin or two, three, or four lectins) selected from a group consisting of MPA, ACA, ABA, and Jacalin.

Note that a structure of the sugar chain can be specified by what kind of lectin it binds with. Therefore, it is sufficient for a "step of determining a level of the sugar chain that binds with ABA," for example, to be a "step of determining a level of the sugar chain having a specific structure that binds with ABA." In other words, a "step of determining a level of the sugar chain that binds with ABA" does not need to be achieved by a lectin assay using ABA. As methods other than a lectin assay, for example, liquid chromatography, mass spectrometry, ELISA, two-dimensional electrophoresis, a protein array, a bead array, flow cytometry, Bio-Plex (registered trademark), and the like can be mentioned.

{1-1-2. Siaα2-6Gal/GalNAc Level Determination Step}

A measurement target in the Siaα2-6Gal/GalNAc level determination step is Siaα2-6Gal/GalNAc. Like Galβ1-3GalNAc, this substance is a sugar chain that is present in living tissue such as renal tissue by being bound with various substances (for example, proteins and lipids). Siaα2-6Gal/GalNAc may also be cut free from the various substances and be present in the sample sampled from the subject. The present inventors also found that patients whose renal disease worsened in the future have a large quantity of Siaα2-6Gal/GalNAc in the above sample, which led to the completion of the present invention.

For description relating to the Siaα2-6Gal/GalNAc level determination step, the above description relating to the Galβ1-3GalNAc level determination step can be referenced.

As examples of glycoproteins having Siaα2-6Gal/GalNAc, alpha 2-HSglycoprotein (AHSG; alias: fetuin-A); orosomucoid 2 (ORM2; aliases: AGP-B, AGP-B', AGP2); alpha-1-microglobulin/bikunin precursor (AMBP; aliases: A1M, EDC1, HCP, HI30, IATIL, ITI, ITIL, ITILC, UTI); serotransferrin (TF; alias: SRPRB); haptoglobin (HP; aliases: BP2ALPHA2, HPA1S); alpha-2-macroglobulin (A2M; aliases: A2MD, CPAMD5, FWP007, S863-7); apolipoprotein A-I (Apoa1; aliases: Alp-1, Apoa-1, Brp-14, Ltw-1, Lvtw-1, Sep-1, Sep-2, Sept, apo-AI, apoA-I); hemopexin (HPX; alias: HX); complement C4A (C4A; aliases: C42, C4A3, C4A4, C4A6, C4AD, C4S, C04, CPAMD2, RG); ceruloplasmin (CP; alias: CP-2); serpin family G member 1 (SERPING1; alias: C1IN, C1NH, C1NH, HAE1, HAE2); alpha-1-B glycoprotein (A1BG); prostaglandin-H2 D-isomerase (MNEG_8879); angiotensinogen (AGT; alias: ANHU, SERPINA8); serpin family C member1 (SERPINC1; alias: AT3); kininogen 1 (KNG1; aliases: BDK, BK, KNG); N-acetylmuramoyl-L-alanine amidase (amiC; aliases: b2817, ECK2813, JW5449, ygdN); complement C3 (C3; aliases: AHUS5, ARMD9, ASPa, C3b, CPAMD1, HEL-S-62p); coagulation factor II, thrombin (F2; aliases: PT, RPRGL2, THPH1); GC, vitamin D binding protein (GC; aliases: DBP, DBP/GC, GRD3, Gc-MAF, GcMAF, HEL-S-51, VDBG, VDBP); microtubule associated scaffold protein 1 (MTUS1; aliases: ATBP, ATIP, ATIP3, ICIS, MP44, MTSG1); insulin-like growth factor binding protein-3 (IGFBP3; aliases: BP-53, IBP3); progestagen associated endometrial protein (PAEP; aliases: GD, GdA, GdF, GdS, PAEG, PEP, PP14); core 1 synthase, glycoprotein-N-acetylgalactosamine 3-beta-galactosyltransferase 1 (C1GALT1; aliases: C1GALT, T-synthase); C1GALT1 specific chaperone 1 (C1GALT1C1; aliases: C1GALT2, C38H2-L1, COSMC, HSPC067, MST143, TNPS); and glucosaminyl (N-acetyl) transferase 1, core 2 (GCNT1; aliases: C2GNT, C2GNT-L, C2GNT1, G6NT, NACGT2, NAGCT2) can be mentioned (see tables 4 and 5).

TABLE 4

| Official gene symbol | Name | Aliases |
| --- | --- | --- |
| AHSG | alpha 2-HS glycoprotein | fetuin-A |
| ORM2 | orosomucoid 2 | AGP-B, AGP-B', AGP2 |
| AMBP | alpha-1-microglobulin/bikunin precursor | AIM, EDC1, HCP, HI30, IATIL, ITI, ITIL, ITILC, UTI |
| TF | serotransferrin | SRPRB |
| HP | haptoglobin | BP2ALPHA2, HPA1S |
| A2M | alpha-2-macroglobulin | A2MD, CPAMD5, FWP007, S863-7 |
| Apoa1 | apolipoprotein A-1 | Alp-1, Apoa-1, Brp-14, Liw-1, Lctw-1, Sep-1, Sep-2, Sep2, apo-AI, apoA-I |
| HPX | hemopexin | HX |
| C4A | complement C4A | C42, C4A3, C4A4, C4A6, C4AD, C4S, CO4, CPAMD2, RG |
| CP | ceruloplasmin | CP-2 |
| SERPING1 | serpin family G member 1 | CHN, CHN4, C1NH, HAE1, HAE2 |
| A1BG | alpha-1-B-glycoprotein | None |
| MNEG_8879 | prostaglamdin-H2 D-isomerase | None |
| AGT | angiotensinogen | ANHU, SERPINA8 |
| SERPINC1 | serpin family C member 1 | AT3 |
| KNG1 | kininogen 1 | BDK, BK, KNG |
| amiC | N-acetylmuramoyl-L-elanine amidase | b2817, ECK2813, JW5449, ygdN |
| C3 | complement C3 | AHUS5, ARMD9, ASPa, C3b, CPAMD1, HEL-S-62p |
| F2 | coagulation factor II, thrombin | PT, RPRGL2, THPH1 |

TABLE 5

| GC | GC, vitamin D binding protein | DBP, DBP/GC, GRD3, Gc-MAF, GeMAF, HEL-S-51, VDBG, VDBP |
| --- | --- | --- |
| MTUS1 | microtubule associated scaffold protein 1 | ATBP, ATIP, ATIP3, ICIS, MP44, MTSG1 |
| IGFBP3 | insululin like growth factor binding protein 3 | BP-53, IBP3 |
| PAEP | progestagen associated endometrial protein | GD, GdA, GdF, GdS, PAEG, PEP, PP14 |

TABLE 5-continued

| | | |
|---|---|---|
| C1GALT1 | core 1 synthase, glcoprotein-N-acetyl-galactosamine 3-beta-galactosyltransferase 1 | C1GALT, T-synthase |
| C1GALT1C1 | C1GALT1 specific chaperone 1 | C1GALT2, C38H2-L1, COSMC, HSPC067, MST143, TNPS |
| GCNT1 | glucosaminyl (N-acetyl) transferase 1, core 2 | C2GNT, C2GNT-L, C2GNT1, G6NT, NACGT2, NAGCT2 |

As examples of the protein involved in converting Siaα2-6Gal/GalNAc, ST6 beta-galactoside alpha-2,6-sialyltransferase 1 (ST6GAL1; aliases: SIAT1, ST6GalI, ST6N), ST3 beta-galactoside alpha-2,3-sialyltransferase 1 (ST3GAL1; aliases: Gal-NAc6S, SIAT4A, SIATFL, ST3GalA, ST3GalA.1, ST3GalIA, ST3GalIA,1, ST30), ST3 beta-galactoside alpha-2,3-sialyltransferase 3 (ST3GAL3; aliases: EIEE15, MRT12, SIAT6, ST3GALII, ST3GalIII, ST3N), ST3 beta-galactoside alpha-2,3-sialyltransferase 4 (ST3GAL4; aliases: CGS23, NANTA3, SAT3, SIAT4, SIAT4C, ST-4, ST3GalA.2, ST3GalIV, STZ, gal-NAc6S), ST6 N-acetylgalactosaminide alpha-2,6-sialyltransferase 1 (ST6GALNAC1; aliases: HSY11339, SIAT7A, ST6GalNAcI, STYI), ST6 N-acetylgalactosaminide alpha-2,6-sialyltransferase 2 (ST6GALNAC2; aliases: SAITL1, SIAT7, SIAT7B, SIATL1, ST6GalNAII, STHM), ST6 N-acetylgalactosaminide alpha-2,6-sialyltransferase 3 (ST6GALNAC3; aliases: PRO7177, SIAT7C, ST6GALNACIII, STY), ST3 beta-galactoside alpha-2,3-sialyltransferase 5 (ST3GAL5; aliases: SATI, SIAT9, SIATGM3S, SPDRS, ST3GalV), ST8 alpha-N-acetyl-neuraminide alpha-2,8-sialyltransferase 1 (ST8SIA1; aliases: GD3S, SIAT8, SIAT8-A, SIAT8A, ST8SiaI), ST3 beta-galactoside alpha-2,3-sialyltransferase 2 (ST3GAL2; aliases: Gal-NAc6S, SIAT4B, ST3GALII, ST3GalA.2), ST8 alpha-N-acetyl-neuraminide alpha-2,8-sialyltransferase 2 (ST8SIA2; aliases: HsT19690, SIAT8-B, SIAT8B,ST8SIA-II, ST8SiaII, STX), ST8 alpha-N-acetyl-neuraminide alpha-2,8-sialyltransferase 3 (ST8SIA3; aliases: SIAT8C, ST8SiaIII), and ST8 alpha-N-acetyl-neuraminide alpha-2,8-sialyltransferase 4 (ST8SIA4; aliases: PST, PST1, SIAT8D, ST8SIA-IV) can be mentioned (see tables 6 and 7).

TABLE 6

| Official gene symbol | Name | Aliases |
|---|---|---|
| ST3GAL1 | ST3 beta-galactoside alpha-2,3-sialyl-transferase 1 | Gal-NAc6S, SIAT4A, SIATFL, ST3GalA, ST3GalA.1, ST3GalIA, ST3GalIA,1.ST30 |
| ST3GAL2 | ST3 beta-galactoside alpha-2,3-sialyl-transferase 2 | Gal-NAc6S, SIAT4B, ST3GALII, ST3GalA.2 |
| ST3GAL3 | ST3 beta-galactoside alpha-2,3-sialyl-transferase 3 | EIEE15, MRT12, SIAT6, ST3GALII, ST3GalIII, ST3N |
| ST3GAL4 | ST3 beta-galactoside alpha-2,3-sialyl-transferase 4 | CGS23, NANTA3, SAT3, SIAT4, SIAT4C, ST-4, ST3GalA.2, ST3GalIV, STZ, gal-NAc6S |
| ST3GAL5 | ST3 beta-galactoside alpha-2,3-sialyl-transferase 5 | SATI, SIAT9, SIATGM3S, SPDRS, ST3GalV |
| ST6GAL1 | ST6 beta-galactoside alpha-2,6-sialyl-transferase 1 | SIAT1, ST6GalII, ST6N |

TABLE 6-continued

| Official gene symbol | Name | Aliases |
|---|---|---|
| ST6GALNAC1 | ST6 N-acetylgalactosamide alpha-2,6-sialyl-transferase 1 | HSY11399, SIAT7A, ST6GalNAeI, STY1 |
| ST6GALNAC2 | ST6 N-acetlygalactosaminide alpha-2,6-sialyl-transferase 2 | SAITL1, SIAT7, SIAT7B, SIATL1, ST6GalNAII, STHM |
| ST6GALNAC3 | ST6 N-acetlygalacto-saminide alpha-2,6-sialyltransferase 3 | PRO7177, SIAT7C, ST6GALNACII, STY |

TABLE 7

| | | |
|---|---|---|
| ST8SIA1 | ST8 alpha-N-acetyl-neuraminide alpha-2,8-sialyltransferase 1 | GD3S, SIAT8, SIAT8-A, SIAT8A, ST8SiaI |
| ST8SIA2 | ST8 alpha-N-acetyl-neuraminide alpha-2,3-sialyltransferase 2 | HsT19690, SIAT8-B, SIAT8B, ST8SIA-II, ST8SiaII, STX |
| ST8SIA3 | ST8 alpha-N-acetyl-neuroaminide alpha-2,3-sialyltransferase 3 | SIAT8C, ST8SiaIII |
| ST8SIA4 | ST8 alpha-N-acetyl-neuraminide alpha-2,3-sialyltransferase 4 | PST, PST1, SIAT8D, ST8SIA-IV |

Note that when the proteins listed above have a plurality of names and/or abbreviations, to identify these, the above databases can be used.

When determining the level of Siaα2-6Gal/GalNAc by a lectin assay, it is preferable to use lectins having binding activity with Siaα2-6Gal/GalNAc. As such lectins, SSA (*Sambucus sieboldiana* lectin; Japanese red elder lectin), SNA (*Sambucus nigra* agglutinin; European elder lectin), and TJA-I (*Trichosanthes japonica* agglutinin I lectin; Chinese snake gourd lectin-I) can be mentioned. These lectins are conventionally known lectins, and amino-acid sequence information thereof is available from various databases.

Of course, as long as a level of a "sugar chain having binding activity with SSA, SNA, and/or TJA-I" can be determined, the Siaα2-6Gal/GalNAc level determination step is not limited to a lectin assay.

As illustrated in the examples described below, the level of Siaα2-6Gal/GalNAc in the sample of the subject can serve as a powerful biomarker for predicting reduced renal function by being combined with existing biomarkers.

{1-2. Other Sugar-Chain Level Determination Steps}

The determination method of one embodiment of the present invention may include, in addition to the above Galβ1-3GalNAc level determination step and/or the Siaα2-6Gal/GalNAc level determination step, a step of determining another sugar-chain level in the sample sampled from the subject. Specifically, the acquisition method of data of one embodiment of the present invention may include a step of determining a level of α-GalNAc, Galα, or Galα1-3Gal (also respectively notated as "α-GalNAc level determination step," "Galα level determination step," and "Galα1-3Gal level determination step"). Only one of these steps may be included, or two or three of these steps may be included. For description of the above steps, the description of the Galβ1-3GalNAc level determination step can be referenced.

As proteins involved in producing, cutting, or converting α-GalNAc, a Gc protein, UDP-N-acetyl-α-D-galactosamine (UDP-GalNAc), α-GalNAc-ase, exostosin-like glycosyltransferase 2 (EXTL2; alias: EXTR2), and glucuronylneolactotetraosylceramide (substrate of α-GalNAc transferase) can be mentioned (see table 8).

TABLE 8

| Official gene symbol | Name | Aliases |
|---|---|---|
| EXTL2 | exostosin like glcosyltransferase 2 | EXTR2 |

As proteins involved in producing, cutting, or converting Galα, insulin-like growth factor 2 receptor (IGF2R; aliases: CD222, CI-M6PR, CIMPR, M6P-R, M6P/IGF2R, MPR 300, MPR1, MPR300, MPR) can be mentioned (see table 9).

TABLE 9

| Official gene symbol | Name | Aliases |
|---|---|---|
| IGF2R | insulin like growth factor 2 receptor | CD222, CI-M6PR, CIMPR, M6P-R, M6P/IGF2R, MPR 300, MPR1, MPR300, MPR |

As proteins involved in producing, cutting, or converting Galα1-3Gal (α-Gal), alpha 1-3-N-acetylgalactosaminyltransferase and alpha 1-3-galactosyltransferase (ABO; aliases: A3GALNT, A3GALT1, GTB, NAGAT), mannosyl (beta-1,4-)-glycoprotein beta-1,4-N-acetylglucosaminyltransferase (MGAT3; aliases: GNT-III, GNT3), ST6 beta-galactoside alpha-2,6-sialyltransferase 1 (ST6GAL1; aliases: SIAT1, ST6GalI, ST6N), and ST3 beta-galactoside alpha-2,3-sialyltransferase 3 (ST3GAL3; aliases: EIEE15, MRT12, SIAT6, ST3GALII, ST3GalIII, ST3N) can be mentioned (see table 10).

TABLE 10

| Official gene symbol | Name | Aliases |
|---|---|---|
| ABO | alpha 1-3-N-acetylgalactosaminyltransferase and alpha 1-3-galactosyltransferase | A3GALNT, A3GALT1, GTB, NAGAT |
| MGAT3 | mannosyl (beta-1,4-)-glycoprotein beta-1,4-N-acetylglucosaminyltransferase | GNT-III, GNT3 |
| ST3GAL3 | ST3 beta-galactoside alpha-2,3-sialyltransferase 3 | EIEE15, MRT12, SIAT6, ST3GALII, ST3GalIII, ST3N |
| ST6GAL1 | ST6 beta-galactoside alpha-2,6-sialyltransferase 1 | SIAT1, ST6GalI, ST6N |

Note that when the proteins listed above have a plurality of names and/or abbreviations, to identify these, the above databases can be used.

When determining the level of α-GalNAc, Galα, or Galα1-3Gal by a lectin assay, it is preferable to respectively use lectins having binding activity with α-GalNAc, Galα, or Galα1-3Gal. As lectins having binding activity with α-GalNAc, VVA (*Vicia villosa* lectin; hairy vetch lectin), HPA (escargot lectin; *Helix pomatia* agglutinin), MPA (Madura *pomifera* agglutinin; Osage orange lectin), PTL_I (*Psophocarpus tetragonolobus* lectin-I; winged bean lectin), GSL_I_A4 (*Griffonia simplicifolia* lectin I A4; bandeiraea bean lectin I A4), and GSL_I_B4 (*Griffonia simplicifolia* lectin I B4; bandeiraea bean I B4) can be mentioned. As lectins having binding activity with Galα, PTL_I (see above), GSL_I_A4 (see above), and GSL_I_B4 (see above) can be mentioned. As a lectin having binding activity with Galα1-3Gal, EEL (*Euonymus europaeus* lectin; spindle lectin) can be mentioned. These lectins are conventionally known lectins, and amino-acid sequence information thereof is available from various databases.

As illustrated in the examples described below, the present inventors found that an increase in binding signals to VVA, EEL, and GSL_I_B4 is negatively correlated to reduced renal function in the future. Moreover, by combining the binding signals to the above lectins and the level of Galβ1-3GalNAc and/or the level of Siaα2-6Gal/GalNAc, a precision of predicting the possibility of reduced renal function in the future significantly increases. Moreover, by combining the binding signals to the above lectins and a factor other than sugar-chain level as well, the precision of predicting the possibility of reduced renal function in the future significantly increases. As such, by the above step of determining the level of the sugar chain binding with the lectins being included, a possibility of the precision of predicting reduced renal function in the future further increasing is anticipated. For similar reasons, by the step of determining the level of at least one type selected from the group consisting of α-GalNAc, Galα, and Galα1-3Gal being included as well, a possibility of the precision of predicting reduced renal function in the future increasing is anticipated.

{1-3. Subject}

In the present specification, "subject" is not limited to a human. The determination method of one embodiment of the present invention can also be applied to a non-human mammal. As the above non-human mammal, an artiodactyl (such as a cow, a wild boar, a pig, a sheep, or a goat), a perissodactyl (such as a horse), a rodent (such as a mouse, a rat, a hamster, or a squirrel), a lagomorph (such as a rabbit), a carnivore (such as a dog, a cat, or a ferret), and the like can be mentioned. The above non-human mammal includes wild animals in addition to livestock or companion animals (pet animals).

In particular, because Galβ1-3GalNAc and Siaα2-6Gal/GalNAc are sugar chains, interspecies structural differences are smaller than in proteins and nucleic acids. Therefore, it is thought that the determination method of one embodiment of the present invention is sufficiently effective as long as it is used with the non-human mammals above.

The above subject is preferably a subject with one or more types of diseases selected from a group consisting of diabetes, hypertension, dyslipidemia, obesity, and hepatic steatosis. Moreover, the above subject is more preferably a subject with diabetes as well as one or more types of diseases selected from a group consisting of hypertension, dyslipidemia, obesity, and hepatic steatosis. This is so (i) cutting Galβ1-3GalNAc and Siaα2-6Gal/GalNAc from a glycoprotein or a glycolipid is increased in the above patient and (ii) cutting of α-GalNAc, Galα, and Galα1-3Gal is attenuated in the above patient.

In the present specification, "diabetes" denotes any disease whose characteristic feature is a state of a glucose concentration in blood or plasma being persistently elevated. That is, the above disease also includes hyperglycemia. In one embodiment, the above diabetes is type 1 diabetes or type 2 diabetes.

{1-4. Sample}

In the present specification, "sample" denotes anything sampled from the subject and is not limited in particular. The above sample includes a lysate of tissue derived from a pathological specimen, a lysate of living tissue, a lysate of cells, and the like in addition to blood, cerebrospinal fluid, lymph, breast milk, saliva, nasal discharge, sweat, urine, stool, and exhaled breath.

In one embodiment of the present invention, the above sample is urine. Making urine the sample is preferable because it is generally used as a biopsy material, other indicators relating to renal function can be simultaneously examined, sampling is easy (particularly when the subject is a human), and the like. As illustrated in the examples described below, this is particularly preferable when the subject is a human because Galβ1-3GalNAc in urine serves as a particularly powerful marker for predicting reduced renal function.

Furthermore, in one embodiment of the present invention, the above sample is blood. Making blood the sample is preferable because it is generally used as a biopsy material, other indicators relating to renal function can be simultaneously examined, sampling is (generally) easy, and the like.

Furthermore, in one embodiment of the present invention, the above sample is renal tissue. For example, by causing lectins to act on a renal tissue sample sampled by a renal biopsy or the like, a distribution of sugar chains corresponding to the above lectins can be visualized and expression levels of the sugar chains corresponding to the lectins can be measured (this method is also referred to as "lectin histochemistry"). By this, not only can reduced renal function be predicted but also diagnosis of a renal disease, determination of a therapeutic effect, and the like can be simultaneously performed.

{1-5. Predicting Reduced Renal Function}

The determination method of one embodiment of the present invention can also be called an acquisition method of data for predicting reduced renal function.

In the present specification, "reduced renal function" denotes a state wherein at least one or more functions associated with the kidney is reduced more than normally anticipated after a certain period from a reference time (for example, when the sample is sampled). Such a state includes, for example, the following types:

1. A renal function that is normally maintained is reduced.
2. A renal function that is normally reduced is reduced more than is normally anticipated.
3. A renal function that is normally improved is improved less than is normally anticipated or is maintained or reduced.

In one embodiment of the present invention, reduced renal function is represented by fluctuations in various indicators relating to renal function. As such indicators, serum creatinine, eGFR (estimated glomerular filtration rate), serum cystatin C, and the like can be mentioned. The above indicators can be measured by normal methods. The eGFR can be calculated by the CKD-EPI equation from, for example, a measurement value of serum creatinine (see Horio, M., et al. [2010], Modifications of the CKD epidemiology collaboration [CKD-EPI] equation for Japanese: accuracy and use for population estimates, *American Journal of Kidney Diseases,* 56[1], 32-38). The eGFR can be calculated according to, for example, a method described in the examples.

Among the above indicators, with serum creatinine, serum urea nitrogen, and serum cystatin C, normally, renal function is determined to be more reduced the greater the measurement value. Normally, with the eGFR, the lower the measurement value, the more reduced renal function is determined to be. The greater an eGFR decline, the greater a reduction rate of renal function is determined to be.

Furthermore, reduced renal function can also be determined based on a difference relationship between the measurement value of an above indicator and a specific reference value (cutoff value). For such a reference value, see for example the description in Japanese Society of Nephrology, ed., *Shīkedi shinryō gaido:* 2012 [CKD Treatment Guide: 2012], Tokyo Igakusha, 2012. Based on this book, for example, the eGFR being less than 60 mL/min/1.73 m$^2$ can be the reference value whereby reduced renal function can be determined.

The reference value relating to the eGFR decline when determining reduced renal function can be, for example, 3 mL/min/1.73 m$^2$/year. This reference value is three times the "normal eGFR decline" indicated in Lindeman, R. D. (1985), Longitudinal studies on the rate of decline in renal function with age, *Journal of the American Geriatrics Society,* 33(4), 278-285 (this is adopted in, for example, Rifkin, D. E. [2008], Rapid kidney function decline and mortality risk in older adults, *Archives of Internal Medicine,* 168[20], 2212-2218).

Another reference value relating to the eGFR decline when determining reduced renal function can be 3 to 5 mL/min/1.73 m$^2$/year (see Coresh, J., et al. [2014], Decline in estimated glomerular filtration rate and subsequent risk of end-stage renal disease and mortality, *The Journal of the American Medical Association,* 311[24], 2518-2531). That is, the above reference value can be made to be 3, 4, or 5 mL/min/1.73 m$^2$/year.

In the examples described below, a group whose eGFR decline is greater than the above reference value is referred to as "eGFR rapid decliners" and a group whose eGFR decline is at or below the above reference value is referred to as "eGFR non-decliners."

In the present specification, "predicting reduced renal function" denotes determining a presence or absence of reduced renal function after a predetermined period (for example, after a predetermined period from sampling the sample). For example, "predicting reduced renal function" denotes performing a determination of "reduced renal function after a predetermined period" or "no reduced renal function after a predetermined period."

In one example, the above "after a predetermined period" can be one month, two months, three months, six months, one year, 1.5 years, two years, 2.5 years, three years, 3.5 years, four years, 4.5 years, five years, six years, seven years, eight years, nine years or ten years after the reference time (for example, when the sample is sampled).

In one embodiment of the present invention, the above prediction result can be a category classification. For example, as a result of the above prediction, a certain subject can be classified as either having "high risk of reduced renal function" or "low risk of reduced renal function." As a more specific example, as a result of the above prediction, a certain subject can be classified as either a "eGFR rapid decliner" or an "eGFR non-decliner."

In another embodiment of the present invention, the above prediction result can be a numerical prediction. For example, as a result of the above prediction, a certain subject can be determined to have "X as a value of a specific indicator (such as the eGFR) indicating renal function after N years." In this example, values of X and N may be numerical ranges having a certain width. The above numerical ranges may be, for example, ranges determined by a statistical method (such as a confidence interval).

Furthermore, based on the above result prediction, a further prediction or determination may be made. This is described below according to the examples described below. First, based on the level of Galβ1-3GalNAc in the sample of a certain subject, it is determined whether this subject is an eGFR rapid decliner. Next, when the above subject is determined to be an eGFR rapid decliner, based on this determination result, it may be determined whether the disease of this subject will worsen, whether dialysis will be necessary after a predetermined period, or the like.

The determination method of one embodiment of the present invention (such as the method described in the examples described below) differs from a conventional method of "examining a pathology of the kidney" (for example, measuring an albumin discharge amount into urine) and can predict reduced renal function. That is, by measuring the level of Galβ1-3GalNAc and/or the level of Siaα2-6Gal/GalNAc in the sample, renal prognosis can be predicted. As such, a renal disease can be treated earlier than by using biomarkers conventionally used in relation to renal disease.

{1-6. Other Aspects}

As another embodiment of the present invention, a determination method including a step of determining a level of a sugar chain that binds with at least one lectin selected from a group consisting of MPA, ACA, ABA, Jacalin, SSA and SNA, VVA, GSL_I_B4, and EEL in a sample sampled from a subject can be mentioned. For description of this aspect, the description of {1-1} to {1-5} is referenced as appropriate.

Note that the determination method of one embodiment of the present invention can also be expressed as follows.

{1} An acquisition method of data for predicting reduced renal function, including a step of determining a level of Galβ1-3GalNAc and/or a level of Siaα2-6Gal/GalNAc in a sample sampled from a subject.

{2} The acquisition method of data of {1}, further including a step of determining a level of at least one type selected from a group consisting of α-GalNAc, Galα, and Galα1-3Gal in the sample sampled from the subject.

{3} The acquisition method of data of {1} or {2}, wherein the step of determining the level of Galβ1-3GalNAc and/or the level of Siaα2-6Gal/GalNAc includes a step of determining a level of a sugar chain that binds with at least one lectin selected from a group consisting of MPA, ACA, ABA, Jacalin, SSA, and SNA.

{4} The acquisition method of data of {2}, wherein the step of determining the level of at least one type of sugar chain selected from the group consisting of α-GalNAc, Galα, and Galα1-3Gal includes a step of determining a level of a sugar chain that binds with at least one lectin selected from a group consisting of VVA, GSL_I_B4, and EEL.

{5} An acquisition method of data for predicting reduced renal function, including a step of determining a level of a sugar chain that binds with at least one lectin selected from a group consisting of MPA, ACA, ABA, Jacalin, SSA, SNA, VVA, GSL_I_B4, and EEL in a sample sampled from a subject.

{6} The acquisition method of data of any one among {1} to {5}, wherein the subject is a subject with one or more types of diseases selected from a group consisting of diabetes, hypertension, dyslipidemia, obesity, and hepatic steatosis.

{2. Kit for Predicting Reduced Renal Function}

{2-1. Lectins Provided in Kit}

A kit of one embodiment of the present invention is provided with lectins that bind with Galβ1-3GalNAc and/or Siaα2-6Gal/GalNAc included in the sample sampled from the subject. As such lectins, the lectins illustrated in {1-1} can be mentioned. As such, description thereof is omitted in this section.

Furthermore, the kit of one embodiment of the present invention may be provided with lectins that bind with at least one type of sugar chain selected from α-GalNAc, Galα, and Galα1-3Gal included in the sample sampled from the subject. As such lectins, the lectins illustrated in {1-2} can be mentioned. As such, description thereof is omitted in this section.

The kit of one embodiment of the present invention may be provided with any one combination of lectins in 1 to 3 below. A kit of another embodiment of the present invention can be one made of only one combination of lectins in 1 to 3 below.

1. A combination of at least one or more lectins (for example, one lectin or two, three, or four lectins) selected from a group consisting of MPA, ACA, ABA, and Jacalin.
2. A combination of at least one or more lectins (for example, one lectin or two, three, four, five, or six lectins) selected from a group consisting of MPA, ACA, ABA, Jacalin, SSA, and SNA.
3. A combination of at least one or more lectins (for example, one lectin or two, three, four, five, six, seven, eight, or nine lectins) selected from a group consisting of MPA, ACA, ABA, Jacalin, SSA, SNA, VVA, GSL_I_B4, and EEL.

As long as it is one made of the combination of lectins in 1 or 2 above, the kit of one embodiment of the present invention can determine the level of Galβ1-3GalNAc and/or the level of Siaα2-6Gal/GalNAc and, as a result, can predict reduced renal function. If it is one made of the combination of lectins in 3 above, in addition to Galβ1-3GalNAc and/or Siaα2-6Gal/GalNAc, the level of at least one type of sugar chain selected from the group consisting of α-GalNAc, Galα, and Galα1-3Gal can be determined and it is anticipated that reduced renal function can be predicted with greater precision.

The lectins provided in the kit of one embodiment of the present invention can be prepared by known methods. Alternatively, commercially available lectins may be used as appropriate.

{2-2. Other Components}

The above lectins may be of a form of being fixed on any substrate. To give one example, the above lectins may be of a form of being fixed on a substrate such as a microarray, an ELISA plate, latex beads, or magnetic beads.

Among the above, the above lectins are preferably fixed on a microarray. With a microarray, when urine is used as the sample, there are advantages of sample concentration being unnecessary and removal of a main protein (such as albumin or IgG) in the sample becoming unnecessary. A fixing method of the lectins on a target can use a known method of fixing a protein on a substrate.

The kit of one embodiment of the present invention may additionally be provided with a drug, a tool, a container, an instruction manual, and the like necessary to use the kit. Moreover, the above drug, tool, container, instruction manual, and the like may adopt an aspect of being obtained separately by a user through the market or telecommunication lines.

The content described in each section above can also be referenced as appropriate in other sections. Moreover, the present invention is not limited to the embodiments above and can be modified in various ways within the scope indicated by the claims. Moreover, embodiments obtained by appropriately combining technical means respectively disclosed in different embodiments are also included in the technical scope of the present invention. Below, the present invention is described in greater detail by the examples, but the present invention is not limited to only these examples.

EXAMPLES

The renal function of diabetes patients was followed over three years to study a correlation thereof with sugar chains included in urine.

{Patient Selection}

Patients for the present study were selected from eight hospitals in Okayama prefecture (Okayama University Hospital, Okayama Medical Center, Okayama Saiseikai General Hospital, Kurashiki Central Hospital, the Sakaibara Heart Institute of Okayama, Tsuyama Chuo Hospital, Japanese Red Cross Okayama Hospital, Okayama City Hospital). Among the type 2 diabetes patients who consented to the present study, 554 patients for whom chronological renal-function data was obtained from 2012 to 2015 were analyzed.

{Measurement of Sugar-Chain Levels by Lectin-Array Analysis}

Using a lectin array (GlycoStation [registered trademark; likewise below] and LecChip [registered trademark; likewise below], made by GlycoTechnica), signal strengths of sugar chains in urine binding with forty-five types of lectins were quantified. In analysis, urine samples from a plurality of patients were analyzed simultaneously.

1. 20 μL of a urine sample and Cy3 mono-reactive dye 100 μg labeling (made by GE Healthcare Life Science) were mixed and reacted in the dark at room temperature for 1 hour.
2. A desalting column (Zeba Desalt Spin Column, made by Thermo Scientific) was centrifuged under conditions of 1,500×g, 1 minute, and 4° C.
3. 300 μL of TBS was passed through the above desalting column. Afterward, the above desalting column was centrifuged under conditions of 1,500×g, 1 minute, and 4° C. and washed. The present step was repeated a total of three times.
4. An entire quantity of the above urine sample and 25 μL of TBS were passed through the above desalting column. Afterward, this was centrifuged under conditions of 1,500×g, 1 minute, and 4° C. to remove unreacted Cy3.
5. After adding 450 μL of a probing solution (made by GlycoTechnica) to the urine sample obtained at 4, 500 μL was measured out.
6. The LecChip was washed three times in the probing solution (100 mL/well per wash). Afterward, the urine-sample solution prepared at 5 was poured into the wells (100 μL/well).
7. The LecChip was reacted for 16 hours or longer at 20° C.
8. The LecChip was measured by a GlycoStation Reader 1200. The measurement was performed in a liquid-phase state wherein the above urine-sample solution is still reacted. Note that measurement conditions were as follows.

Exposure time: 299 milliseconds; camera gain: 95.

9. Measurement values were quantified by GlycoStation ToolsPro Suite 1.5.
10. Values obtained by subtracting a background signal value from signal strengths of each lectin were defined as sugar-chain signals for each lectin and used for analysis.

{Main Clinical Parameters and Definitions Thereof}

The date in 2011 (Apr. 1, 2011, to Mar. 31, 2012) when a blood test and a urine test were executed was established as a reference date.

Starting from the above reference date, the following information was collected each year:

Age

Sex

BMI

Ambulatory blood pressure

Abdominal circumference

Presence or absence and severity of diabetic retinopathy (simple diabetic retinopathy, pre-proliferative diabetic retinopathy, or proliferative diabetic retinopathy)

Treatment details (use of an antihypertensive, use of an antidiabetic or insulin, use of an antihyperlipidemic, use of an antihyperuricemic)

HbA1c (NGSP value)

Serum creatinine

UACR.

An eGFR (mL/min/1.73 m$^2$) was calculated by the CKD-EPI equation from a measurement value of serum creatinine (see Horio, M., et al. [2010], Modification of the CKD epidemiology collaboration [CKD-EPI] equation for Japanese: accuracy and use for population estimates, *American Journal of Kidney Diseases*, 56[1], 32-38).

The eGFR was calculated from the measurement values of serum creatinine measured every year for a total of four times from 2011 to 2013, and next, a linear regression line was derived from the calculated eGFRs. The slope of the above linear regression line (that is, an eGFR decline in one year [mL/min/1.73 m$^2$/year]) was made to be the eGFR decline.

A group whose eGFR decline was over 3 mL/min/1.73 m$^2$/year was defined as eGFR rapid decliners, and a group whose eGFR decline was 3 mL/min/1.73 m$^2$/year or less was defined as eGFR non-decliners. This cutoff value is based on the cutoff-value study results reported in Coresh, J., et al. (2014), Decline in estimated glomerular filtration rate and subsequent risk of end-stage renal disease and mortality, *The Journal of the American Medical Association*, 311(24), 2518-2531. This paper categorizes patients whose eGFR on a reference date is 60 mL/min/1.73 m$^2$ or greater according to eGFR decline and compares population-attributable risks by a three-year follow-up. As a result, patients belonging to a category of 3 to 5 mL/min/1.73 m$^2$/year had the highest population-attributable risk of end-stage renal disease (ESRD).

Furthermore, in other reported literature as well, predictors of eGFR rapid decliners are studied with an eGFR decline of 3 mL/min/1.73 m$^2$/year or greater as the cutoff value (for example, see Rifkin, D. E. [2008], Rapid kidney function decline and mortality risk in older adults, *Archives of Internal Medicine*, 168[20], 2212-2218, and Moriya, T., et al. [2017], Patients with type 2 diabetes having higher glomerular filtration rate showed rapid renal function decline followed by impaired glomerular filtration rate: Japan Diabetes Complications study, *Journal of Diabetes and Its Complications*, 31[2], 473-478). Therefore, in the present study as well, 3 mL/min/1.73 m$^2$/year was made to be the cutoff value of eGFR decline.

As for the UACR (mg/g Cr), UACR<30 was defined to be normoalbuminuria, 30 UACR<300 was defined to be microalbuminuria, and UACR 300 was defined to be overt albuminuria. This classification standard is according to KDOQI (2007), KDOQI clinical practice guidelines and clinical practice recommendations for diabetes and 12-S154 chronic kidney disease, *American Journal of Kidney Diseases*, 49 (issue 2, suppl. 2), S12-S154.

The measurement values of each type of sugar-chain signal were used in analysis by being converted into $1/1{,}000$, $1/10{,}000$, or a logarithm according to distribution and/or value. The measurement values of the UACR were used in analysis by being converted into a natural logarithm.

{Analysis}

Analysis relating to the relationship between the sugar-chain signals and reduced renal function was performed for the following two types of variables:

1. eGFR decline (continuous variable)
2. Categorization into eGFR rapid decliners or eGFR non-decliners (binary variable).

The analysis of 1 studied the relationship between eGFR decline and sugar-chain signal strength by single-regression analysis and multiple-regression analysis. In single-regression analysis, the dependent variable was defined as the eGFR decline (continuous variable) and the independent variables were defined as the signal strengths of the sugar chains binding with each type of lectin. In multiple-regression analysis, age, sex, BMI, central arterial pressure (MAP), HbA1c (NGSP value), eGFR, and log UACR were further added as the independent variables (all values on the reference date). Multiple-regression analysis can evaluate an effect of the signal strengths of the sugar chains that bind with each type of lectin on the eGFR decline after effects of the other independent variables are removed.

The analysis of 2 studied sugar-chain signals suited to distinguishing between eGFR rapid decliners and eGFR non-decliners by univariate logistic regression analysis and multivariate logistic regression analysis. In univariate logistic regression analysis, the dependent variable was defined as a value of (eGFR rapid decliners/eGFR non-decliners) and the independent variables were defined as the signal strengths of the sugar chains that bind with each type of lectin. In multivariate logistic regression analysis, age, sex, BMI, central arterial pressure (MAP), HbA1c (NGSP value), eGFR, and log UACR were further added as the independent variables (all values on the reference date). Additionally, an odds ratio for the eGFR rapid decliners of when the signal strengths of the sugar chains that bind with each type of lectin increase by 1 SD (standard deviation) was sought. Multivariate logistic regression analysis can evaluate an effect of the signal strengths of the sugar chains that bind with each type of lectin on determining eGFR rapid decliners and eGFR non-decliners after effects of the other independent variables are removed.

Furthermore, for lectin-binding sugar-chain signals exhibiting usefulness in the analyses of 1 and 2, how much of an additional effect is imparted to the ability of existing biomarkers to predict rapid renal-function decliners was studied by the following procedures.

A multivariate logistic regression model using age, sex, BMI, central arterial pressure (MAP), HbA1c (NGSP value) eGFR, and log UACR (all values on the reference date) was made to be a reference model. Regression models that adds each lectin-binding sugar-chain signal exhibiting usefulness according to the analyses of 1 and 2 to the above reference model are created, and C-indices of each regression model are compared. A usefulness of an additional effect by each lectin-binding sugar chain is studied according to whether a difference in the C-indices is significant and a value of NRI (net reclassification improvement).

Here, the higher the value of the C-index, the more accurately the eGFR rapid decliners and the eGFR non-decliners are determined. Moreover, NRI is an indicator of improvement in diagnostic ability by adding new biomarkers, and a higher value represents a higher diagnostic ability (see Pencina, M. J., et al. [2011], Extensions of net reclassification improvement calculations to measure usefulness of new biomarkers, *Statistics in Medicine*, 30[1], 11-21).

The analyses described above were all performed using Stata SE software (version 14.0, made by StataCorp LP).

{Results}

{Result 1: Patient Background}

Table 11 indicates the total number of patients and patient backgrounds on the reference date for eGFR rapid decliners and eGFR non-decliners.

TABLE 11

| Main clinical factors | All patients (n = 554) | Non decliner (n = 450) | Rapid decliner (n = 104) | P-value |
|---|---|---|---|---|
| Male (%) | 59 | 58 | 63 | 0.35 |
| Age (years) | 63 ± 11 | 64 ± 11 | 62 ± 12 | 0.19 |
| BMI (kg/m$^2$) | 25.6 ± 4.5 | 25.5 ± 4.3 | 25.9 ± 5.2 | 0.41 |
| Est. diabetes duration (years)* (n = 534) | 11.0 (6.2-17.7) | 11.1 (6.8-17.1) | 10.4 (5.4-19.6) | 0.75 |
| Systolic blood pressure (mmHg) | 130.6 ± 16.1 | 129.8 ± 15.7 | 134.4 ± 17.4 | <0.01 |
| Diastolic blood pressure (mmHg) | 74.7 ± 10.7 | 74.1 ± 10.2 | 77.1 ± 12.4 | 0.02 |
| Mean arterial pressure (mmHg) | 93.3 ± 11.2 | 92.7 ± 10.8 | 96.2 ± 12.8 | <0.01 |
| Hypertension** (%) | 70 | 67 | 81 | <0.01 |
| Diabetic retinopathy (n = 512) (NDR/SDR/prePDR/ PDR %) | 66/18/6/10 | 67/19/6/8 | 63/16/6/16 | 0.18 |
| eGFR (ml/min/1.73 m$^2$) | 72.1 ± 16.3 | 73.47 ± 15.2 | 65.4 ± 19.0 | <0.001 |
| CKD G1/G2/G3/G4 (%) | 10/72/16/2 | 11/14/14/1 | 5/63/26/7 | <0.001 |
| UACR (mg/gCr)* | 16.6 (7.6-61.8) | 15.2 (7.4-49.4) | 35.3 (11.0-506.6) | <0.001 |

TABLE 11-continued

| Main clinical factors | All patients (n = 554) | Non decliner (n = 450) | Rapid decliner (n = 104) | P-value |
|---|---|---|---|---|
| Normo/Micro/Macro (%) | 64/25/11 | 68/26/6 | 48/22/30 | <0.001 |
| HbA1c (%) | 7.1 ± 1.1 | 7.1 ± 1.0 | 7.1 ± 1.3 | 0.31 |
| Antidiabetic (No/OHA/Insulin, %) | 4/64/32 | 4/65/31 | 4/59/37 | 0.50 |
| ACE-I or ARB (%) (n = 530) | 51 | 48 | 61 | 0.03 |
| History of CVD (%) | 26 | 26 | 29 | 0.47 |

Abbreviations:
BMI: body mass index;
NDR: no diabetic retinopathy;
SDR: simple retinopathy;
prePDR: pre-proliferative retinopathy;
PDR: proliferative retinopathy;
CKD: chronic kidney disease;
UACR: urinary albumin-to-creatine ratio;
Normo: normoalbuminuria;
Micro: microalbuminuria;
Macro: macroalbuminuira,
OHA: only oral hypoglycemic agent;
Insulin: use of insulin;
ACE-1 or ARB: use of angiotensin-converting enzyme inhibitor or use of angiotensin II receptor blocker;
CVD: cardiovascular event (angina, myocardial infarction, cerebral infarction, cerebral hemorrhage, arteriosclerosis obliterans; each being symptomatic)
*Median (interquartile range)
**Hypertension is defined as at least one antihypertensive being taken or systolic blood pressure > 140 or diastolic blood pressure > 90 on the reference date.

The percentage of men among all patients was 59%, the average age was 63, and the average BMI was 25.6 (kg/m$^2$). As for the medical histories of all patients, the median of estimated duration of diabetes was 11.0 years, the percentage of diabetic retinopathy was 34%, and the percentage of hypertension was 70%. As for the renal function of all patients, the eGFR was 72.1±16.3 mL/min/1.73 m$^2$, the median of the UACR was 16.6 mg/g Cr (in terms of an interquartile range, 7.6 to 61.8; percentages of microalbuminuria and macroalbuminuria respectively 25% and 11%), and HbA1c was 7.1%. As for blood-sugar control of all patients, 64% of patients used only an oral hypoglycemic agent and 32% of patients used insulin. As for use of an antihypertensive among all patients, a usage percentage of an ACE-I (angiotensin-converting enzyme inhibitor) or an ARB (angiotensin II receptor blocker) was 51%.

As is clear from table 1, comparing the eGFR rapid decliner group against the eGFR non-decliner group, the eGFR of the former was significantly lower on the reference date and the UACR was significantly higher. Likewise, comparing the eGFR rapid decliner group against the eGFR non-decliner group, systolic blood pressure, diastolic blood pressure, mean arterial pressure, and percentage of hypertension on the reference date were significantly higher. However, in both groups, no significant difference was recognized in relation to HbA1c and diabetes treatment (usage percentage of an oral hypoglycemic agent or insulin) on the reference date.

Figure 1:
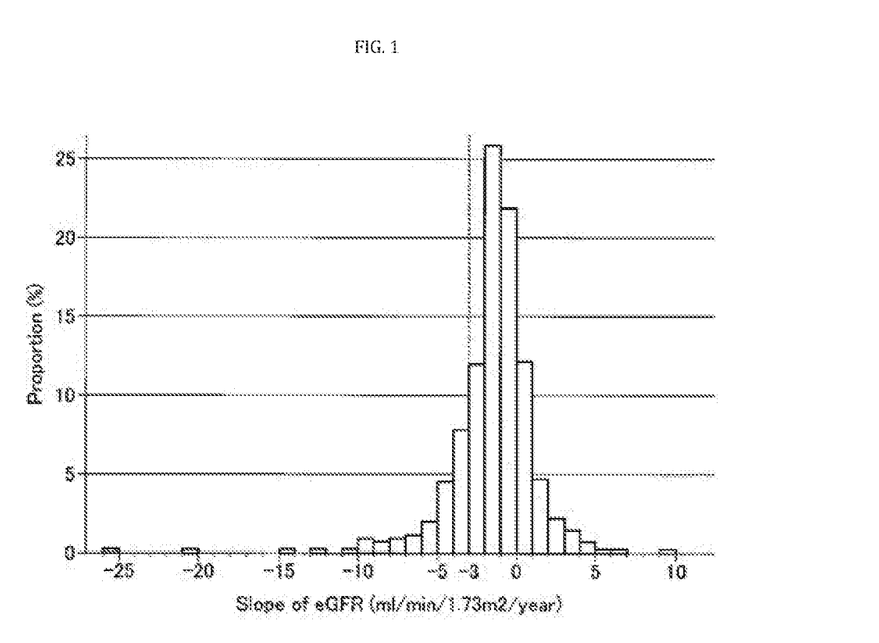
FIG. 1 A histogram representing a distribution of eGFR change rates three years after starting measurement of 554 patients analyzed in the examples.

FIG. 1 illustrates a distribution of the eGFR declines of all patients. A percentage of patients for which the slope of the linear regression line sought from the calculated eGFR is −2 to 0 (patients whose eGFR decline is 0 to 2 mL/min/1.73 m$^2$/year) was large, and the percentage of eGFR rapid decliners (3 mL/min/1.73 m$^2$/year) was 19%.

{Result 2: Analysis Results of eGFR as Continuous Variable}

Figure 2:
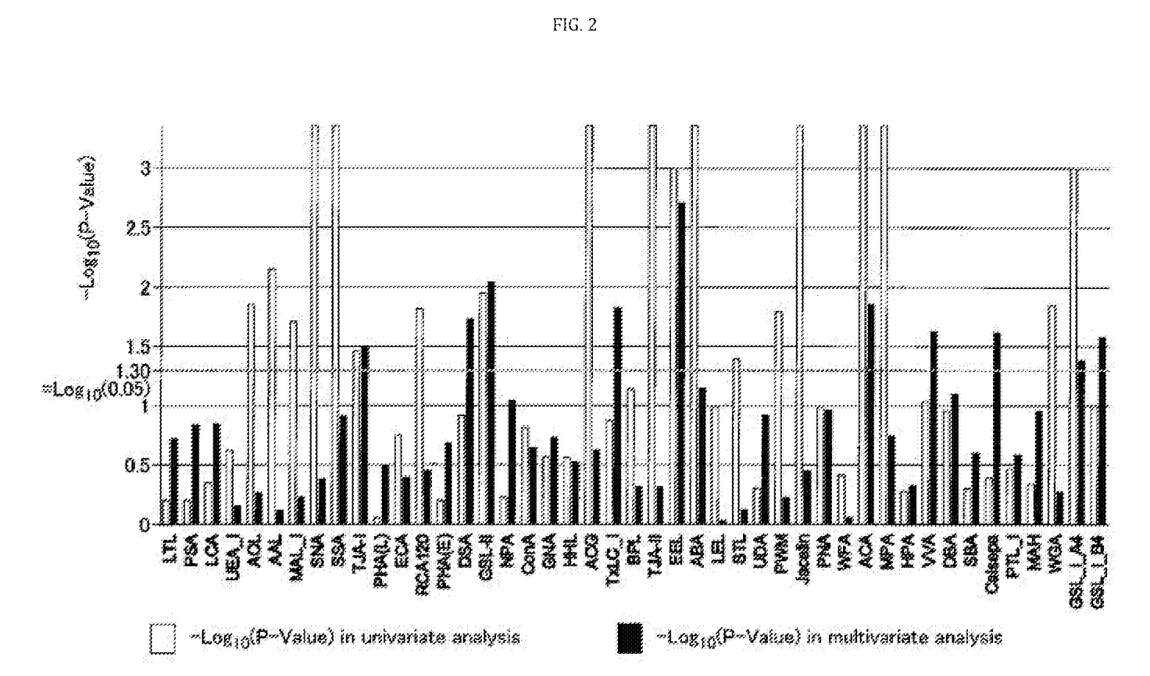
FIG. 2 A graph evaluating a correlation between levels of sugar chains that bind with forty-five types of lectins and eGFR decline according to a P value.

Table 12 and FIG. 2 illustrate results of studying a relationship between eGFR decline and sugar-chain signal strength by single regression analysis and multiple regression analysis.

TABLE 12

| Lectin | Single regression analysis | | Multiple regression analysis | |
|---|---|---|---|---|
| | β coefficient | P value | β coefficient | P value |
| LTL | 0.02 | 0.62 | 0.05 | 0.19 |
| PSA | −0.02 | 0.63 | 0.06 | 0.15 |
| LCA | −0.03 | 0.44 | 0.06 | 0.14 |
| UEA_I | −0.05 | 0.23 | 0.02 | 0.69 |
| AOI | −0.10 | 0.014 | 0.03 | 0.55 |
| AAL | 0.12 | 0.007 | −0.01 | 0.77 |
| MAL_I | −0.10 | 0.019 | −0.02 | 0.59 |
| SNA | −0.23 | <0.001 | −0.04 | 0.42 |
| SSA | −0.25 | <0.001 | −0.08 | 0.12 |
| TJA-I | −0.09 | 0.034 | 0.10 | 0.032 |
| PHA(L) | 0.01 | 0.87 | 0.04 | 0.32 |
| ECA | −0.06 | 0.18 | 0.03 | 0.41 |
| RCA120 | −0.10 | 0.015 | 0.04 | 0.35 |
| PHA(E) | −0.02 | 0.64 | 0.05 | 0.21 |
| DSA | 0.07 | 0.12 | 0.10 | 0.018 |
| GSL-II | 0.11 | 0.011 | 0.11 | 0.009 |
| NPA | −0.02 | 0.59 | 0.07 | 0.09 |
| ConA | −0.06 | 0.15 | 0.05 | 0.23 |
| GNA | 0.05 | 0.26 | 0.05 | 0.20 |
| HHL | −0.05 | 0.27 | 0.04 | 0.30 |
| ACG | −0.15 | <0.001 | −0.05 | 0.24 |
| TxLC_1 | −0.02 | 0.60 | 0.10 | 0.015 |
| BPL | −0.08 | 0.07 | 0.01 | 0.82 |
| TJA-II | −0.16 | <0.001 | −0.03 | 0.51 |
| EFK | 0.15 | 0.001 | 0.13 | 0.002 |
| ABA | −0.16 | <0.001 | −0.08 | 0.07 |
| LEL | −0.07 | 0.1 | −0.003 | 0.94 |
| STL | −0.09 | 0.041 | −0.01 | 0.76 |
| UDA | −0.03 | 0.49 | 0.06 | 0.12 |
| PWM | −0.10 | 0.016 | −0.02 | 0.60 |
| Jacalin | .016 | <0.001 | −0.04 | 0.36 |
| PNA | 0.07 | 0.1 | 0.07 | 0.11 |
| WFA | −0.04 | 0.38 | 0.01 | 0.89 |
| ACA | −0.24 | <0.001 | −0.11 | 0.014 |
| MPA | −0.17 | <0.001 | −0.06 | 0.18 |
| HPA | −0.03 | 0.53 | 0.03 | 0.48 |
| VVA | 0.07 | 0.09 | 0.09 | 0.023 |
| DBA | 0.07 | 0.11 | 0.07 | 0.08 |
| SBA | 0.03 | 0.50 | 0.05 | 0.25 |
| Calsepe | −0.04 | 0.41 | 0.10 | 0.024 |
| PTL_1 | 0.04 | 0.34 | 0.04 | 0.26 |
| MAH | 0.03 | 0.45 | 0.06 | 0.11 |

TABLE 12-continued

| Lectin | Single regression analysis | | Multiple regression analysis | |
|---|---|---|---|---|
| | β coefficient | P value | β coefficient | P value |
| WGA | −0.10 | 0.014 | −0.03 | 0.53 |
| GSL_I_A4 | 0.14 | 0.001 | 0.08 | 0.041 |
| GSL_I_B4 | 0.07 | 0.10 | 0.09 | 0.026 |

When the eGFR decline is made to be a continuous variable, significantly related sugar chains in both single regression analysis and multiple regression analysis were ACA-binding sugar chains, EEL-binding sugar chains, GSL-II-binding sugar chains, and GSL_I_A4-binding sugar chains (P=0.05 being the standard of significant difference). As the signal strengths of the ACA-binding sugar chains increased and as the signal strengths of the EEL-binding sugar chains, the GSL-II-binding sugar chains, and the GSL_I_A4-binding sugar chains decreased, indicators indicating eGFR decline increased. β coefficients in multiple regression analysis of the above sugar-chain signal strengths were respectively −0.11, 0.13, 0.11, and 0.08.

The above results suggest that the signal strengths of the ACA-binding sugar chains, the EEL-binding sugar chains, and the GSL-II-binding sugar chains can serve as strong renal prognosis factors independent from eGFR and UACR.

{Result 3: Analysis Results of Category Classification into eGFR Rapid Decliners/eGFR Non-Decliners}

Figure 3:
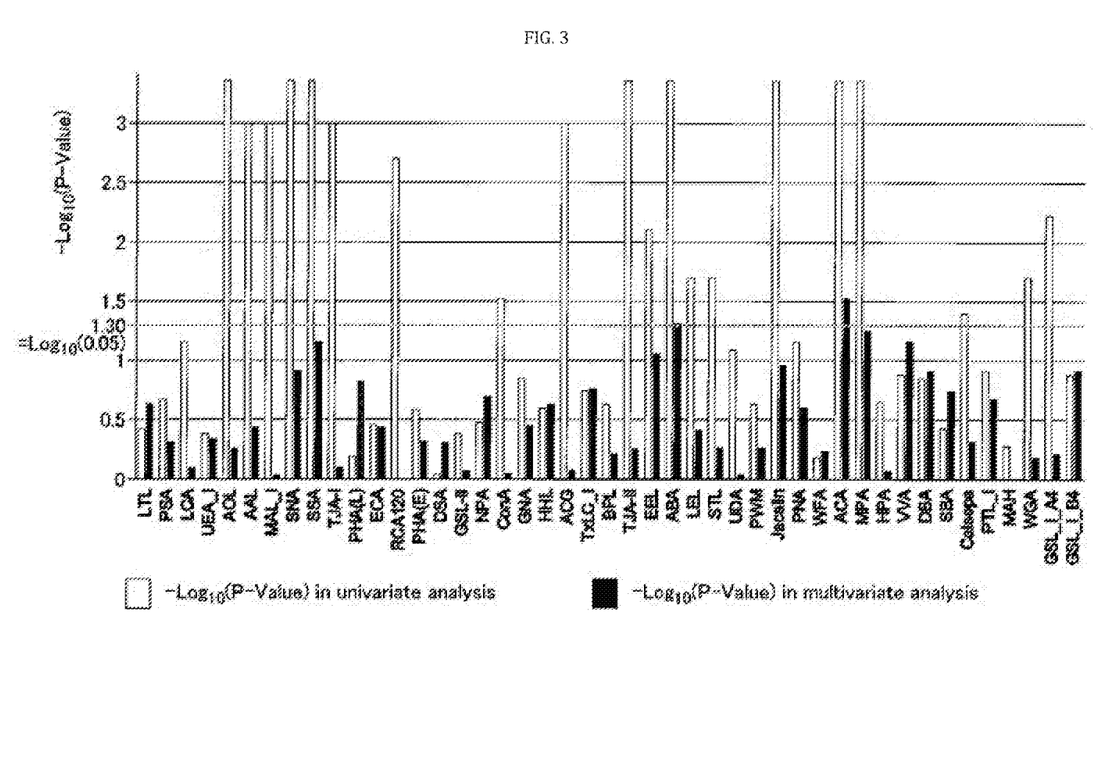
FIG. 3 A graph evaluating a correlation between levels of sugar chains that bind with forty-five types of lectins and eGFR rapid decliners according to a P value.

Table 13 and FIG. 3 illustrate results of studying a relationship between the value of (eGFR rapid decliners/eGFR non-decliners) and sugar-chain signal strength by univariate logistic regression analysis and multivariate logistic regression analysis.

TABLE 13

| Lectin | Univariate logistic | | Multivariate logistic | |
|---|---|---|---|---|
| | Odds ratio (95% CI) | P-value | Odds ratio (95% CI) | P-value |
| LTL | 0.91 (0.74-1.12) | 0.37 | 0.87 (0.70-1.09) | 0.23 |
| PSA | 1.15 (0.92-1.44) | 0.21 | 0.92 (0.72-1.17) | 0.48 |
| LCA | 1.24 (0.99-1.56) | 0.07 | 0.96 (0.75-1.23) | 0.78 |
| UEA_I | 1.11 (0.87-1.40) | 0.40 | 0.92 (0.74-1.14) | 0.45 |
| AOI | 1.45 (1.18-1.78) | <0.001 | 1.07 (0.84-1.37) | 0.56 |
| AAL | 1.49 (1.17-1.89) | 0.001 | 1.13 (0.87-1.46) | 0.36 |
| MAL_I | 1.49 (1.17-1.89) | 0.001 | 0.99 (0.78-1.26) | 0.92 |
| SNA | 1.73 (1.41-2.12) | <0.001 | 1.24 (0.95-1.62) | 0.12 |
| SSA | 1.78 (1.45-2.18) | <0.001 | 1.29 (0.98-1.70) | 0.07 |
| TJA-I | 1.42 (1.15-1.75) | 0.001 | 0.96 (0.74-1.25) | 0.77 |
| PHA(L) | 0.95 (0.77-1.18) | 0.64 | 0.84 (0.66-1.06) | 0.15 |
| ECA | 1.12 (0.89-1.41) | 0.34 | 0.89 (0.70-1.13) | 0.37 |
| RCA120 | 1.39 (1.13-1.71) | 0.002 | 1.00 (0.78-1.29) | 0.99 |
| PHA(E) | 1.13 (0.92-1.40) | 0.25 | 0.91 (0.72-1.17) | 0.47 |
| DSA | 1.01 (0.82-1.26) | 0.89 | 0.92 (0.73-1.17) | 0.49 |
| GSL-II | 0.92 (0.75-1.13) | 0.41 | 0.98 (0.78-1.22) | 0.83 |
| NPA | 1.12 (0.90-1.39) | 0.33 | 0.85 (0.67-1.09) | 0.20 |
| ConA | 1.29 (1.03-1.63) | 0.03 | 0.98 (0.76-1.27) | 0.87 |
| GNA | 1.18 (0.95-1.48) | 0.14 | 0.89 (0.70-1.14) | 0.35 |
| HHL | 1.14 (0.91-1.42) | 0.25 | 0.86 (0.67-1.10) | 0.23 |
| ACG | 1.40 (1.15-1.72) | 0.001 | 1.03 (0.80-1.32) | 0.82 |
| TxLC_I | 1.16 (0.94-1.43) | 0.18 | 0.83 (0.64-1.08) | 0.17 |
| BPL | 1.14 (0.92-1.40) | 0.23 | 0.94 (0.74-1.19) | 0.61 |
| TJA-II | 1.45 (1.19-1.78) | <0.001 | 1.08 (0.84-1.38) | 0.35 |
| EEL | 0.77 (0.64-0.94) | 0.008 | 0.84 (0.68-1.03) | 0.09 |
| ABA | 1.61 (1.26-2.06) | <0.001 | 1.28 (1.00-1.64) | 0.049 |
| LEL | 1.29 (1.05-1.59) | 0.02 | 1.11 (0.88-1.40) | 0.38 |
| STL | 1.27 (1.03-1.57) | 0.02 | 1.08 (0.85-1.36) | 0.54 |
| UDA | 1.21 (0.98-1.50) | 0.08 | 0.98 (0.77-1.25) | 0.90 |
| PWM | 1.16 (0.91-1.47) | 0.23 | 0.93 (0.75-1.16) | 0.53 |
| Jacalin | 1.62 (1.29-2.05) | <0.001 | 1.25 (0.95-1.63) | 0.11 |
| PNA | 0.84 (0.70-1.02) | 0.07 | 0.88 (0.72-1.09) | 0.24 |
| WFA | 1.05 (0.85-1.31) | 0.64 | 0.94 (0.74-1.18) | 0.57 |

TABLE 13-continued

| Lectin | Univariate logistic | | Multivariate logistic | |
|---|---|---|---|---|
| | Odds ratio (95% CI) | P-value | Odds ratio (95% CI) | P-value |
| ACA | 1.67 (1.37-2.04) | <0.001 | 1.31 (1.02-1.67) | 0.03 |
| MPA | 1.55 (1.27-1.89) | <0.001 | 1.25 (1.00-1.59) | 0.049 |
| HPA | 1.15 (0.92-1.45) | 0.22 | 0.98 (0.77-1.23) | 0.84 |
| VVA | 0.84 (0.67-1.05) | 0.13 | 0.80 (0.63-1.02) | 0.07 |
| DBA | 0.85 (0.68-1.06) | 0.14 | 0.82 (0.65-1.05) | 0.12 |
| SBA | 0.90 (0.73-1.13) | 0.37 | 0.85 (0.67-1.08) | 0.18 |
| Calsepe | 1.25 (1.01-1.54) | 0.04 | 0.91 (0.71-1.17) | 0.47 |
| PTL_1 | 0.85 (0.70-1.04) | 0.12 | 0.87 (0.70-1.08) | 0.21 |
| MAH | 1.08 (0.85-1.37) | 0.52 | 1.00 (0.81-1.24) | 0.98 |
| WGA | 1.28 (1.04-1.58) | 0.02 | 1.06 (0.84-1.33) | 0.65 |
| GSL_I_A4 | 0.77 (0.64-0.93) | 0.006 | 0.94 (0.76-1.17) | 0.60 |
| GSL_I_B4 | 0.85 (0.69-1.05) | 0.13 | 0.83 (0.66-1.05) | 0.12 |

In both univariate logistic regression analysis and multivariate logistic regression analysis, sugar chains significantly related to eGFR rapid decliners were ABA-binding sugar chains, ACA-binding sugar chains, and MPA-binding sugar chains. Although SNA-binding sugar chains, SSA-binding sugar chains, Jacalin-binding sugar chains, and EEL-binding sugar chains were recognized to have a strong correlation in univariate logistic regression analysis, they did not exhibit statistical significance in multivariate logistic regression analysis. Conversely, although WA-binding sugar chains did not exhibit significance in univariate logistic regression analysis, strong correlation was recognized in multivariate logistic regression analysis.

Odds ratios (95% confidence interval) for the eGFR rapid decliners of when each lectin-binding sugar-chain signal strength above increases by 1 SD (standard deviation) according to a multivariate logistic regression model corrected by eGFR, UACR, and the like were respectively ABA-binding sugar chains: 1.28 (1.00 to 1.64), ACA-binding sugar chains: 1.31 (1.02 to 1.67), MPA-binding sugar chains: 1.25 (1.00 to 1.59), Jacalin-binding sugar chains: 1.25 (0.95 to 1.63), SNA-binding sugar chains: 1.24 (0.95 to 1.62), SSA-binding sugar chains: 1.29 (0.98 to 1.70), EEL-binding sugar chains: 0.84 (0.68 to 1.03), and VVA-binding sugar chains: 0.80 (0.63 to 1.02). That is, with the ABA-binding sugar chains, the ACA-binding sugar chains, the MPA-binding sugar chains, the Jacalin-binding sugar chains, the SNA-binding sugar chains, and the SSA-binding sugar chains, as the signal strength increases, the indicator indicating a relationship with eGFR rapid decliners increases. Meanwhile, with the EEL-binding sugar chains and the WA-binding sugar chains, as the signal strength decreases, the indicator indicating a relationship with eGFR rapid decliners increases. This suggests that each of these signal strengths can serve as a strong renal prognosis factor independent from eGFR and UACR.

This suggests that, in particular, signal strengths of ABA-binding sugar chains, ACA-binding sugar chains, and MPA-binding sugar chains can serve as strong renal prognosis factors independent from eGFR and UACR.

{Result 4: Relationship Between MPA-Binding Sugar Chains, ACA-Binding Sugar Chains, ABA-Binding Sugar Chains, Jacalin-Binding Sugar Chains, SSA-Binding Sugar Chains, SNA-Binding Sugar Chains, WA-Binding Sugar Chains, GSL_I_B4-Binding Sugar Chains, and EEL-Binding Sugar Chains and eGFR Rapid Decliners}

In light of the above results, MPA-binding sugar chains, ACA-binding sugar chains, ABA-binding sugar chains, Jacalin-binding sugar chains, SSA-binding sugar chains, SNA-binding sugar chains, WA-binding sugar chains, GSL_I_B4-binding sugar chains, and EEL-binding sugar chains were focused on as useful factors in predicting eGFR rapid decliners. As such, signal strengths of the above sugar chains were classified into quartiles to perform logistic regression analysis similar to analysis 2. Results are indicated in tables 14 to 16.

TABLE 14

| | Odds ratio (95% confidence interval) | |
|---|---|---|
| Sugar chain | Univariate logistic | Multivariate logistic |
| MPA-binding sugar chains | | |
| First group | Reference | Reference |
| Second group | 1.15 (0.56-2.37) | 1.38 (0.66-2.92) |
| Third group | 2.03 (1.05-3.93) | 1.87 (0.93-3.77) |
| Fourth group | 3.25 (1.72-6.14) | 2.41 (1.20-4.87) |
| Per SD | 1.55 (1.27-1.89) | 1.26 (1.00-1.60) |
| ACA-binding sugar chains | | |
| First group | Reference | Reference |
| Second group | 1.21 (0.59-2.46) | 1.23 (0.58-2.58) |
| Third group | 1.77 (0.90-3.47) | 1.82 (0.90-3.68) |
| Fourth group | 3.42 (1.81-6.43) | 2.10 (1.02-4.31) |
| Per SD | 1.67 (1.37-2.04) | 1.31 (1.02-1.67) |
| ABA-binding sugar chains | | |
| First group | Reference | Reference |
| Second group | 1.13 (0.55-2.33) | 1.07 (0.51-2.27) |
| Third group | 1.69 (0.86-3.32) | 1.63 (0.80-3.31) |
| Fourth group | 3.65 (1.94-6.86) | 2.32 (1.14-4.73) |
| Per SD | 1.61 (1.26-2.06) | 1.28 (1.00-1.64) |
| Jacalin-binding sugar chains | | |
| First group | Reference | Reference |
| Second group | 0.94 (0.46-1.91) | 1.01 (0.49-2.10) |
| Third group | 1.63 (0.85-3.13) | 1.49 (0.75-2.96) |
| Fourth group | 2.91 (1.58-5.37) | 1.82 (0.90-3.70) |
| Per SD | 1.28 (1.03-1.59) | 1.09 (0.95-1.27) |

TABLE 15

| SSA-binding sugar chains | | |
|---|---|---|
| First group | Reference | Reference |
| Second group | 1.80 (0.90-3.58) | 1.69 (0.83-3.44) |
| Third group | 1.31 (0.64-2.70) | 1.09 (0.50-2.32) |
| Fourth group | 3.93 (2.06-7.47) | 1.92 (0.90-4.13) |
| Per SD | 1.78 (1.45-2.18) | 1.29 (0.98-1.70) |
| SNA-binding sugar chains | | |
| First group | Reference | Reference |
| Second group | 1.63 (0.81-3.27) | 1.57 (0.76-3.25) |
| Third group | 1.81 (0.91-3.61) | 1.46 (0.70-3.03) |
| Fourth group | 3.43 (1.79-6.56) | 1.50 (0.70-3.24) |
| Per SD | 1.73 (1.41-2.12) | 1.24 (0.95-1.62) |

TABLE 16

| VVA-binding sugar chains | | |
|---|---|---|
| First group | Reference | Reference |
| Second group | 1.57 (0.87-2.81) | 1.63 (0.85-3.11) |
| Third group | 1.11 (0.64-2.05) | 1.21 (0.62-2.35) |
| Fourth group | 0.81 (0.42-1.54) | 0.71 (0.35-1.46) |
| Per SD | 0.84 (0.67-1.05) | 0.80 (0.63-1.02) |
| GSL_I_B4-binding sugar chains | | |
| First group | Reference | Reference |
| Second group | 0.93 (0.53-1.61) | 0.97 (0.52-1.72) |
| Third group | 0.59 (0.33-1.08) | 0.70 (0.37-1.34) |
| Fourth group | 0.52 (0.28-0.97) | 0.42 (0.21-0.85) |
| Per SD | 0.85 (0.69-1.05) | 0.83 (0.66-1.05) |
| EEL-binding sugar chains | | |
| First group | Reference | Reference |
| Second group | 0.65 (0.35-1.21) | 0.92 (0.48-1.78) |
| Third group | 0.92 (0.52-1.65) | 0.97 (0.52-1.81) |
| Fourth group | 0.80 (0.44-1.44) | 0.69 (0.35-1.34) |
| Per SD | 0.77 (0.64-0.94) | 0.84 (0.68-1.03) |

Quartile groups in each sugar-chain modification signal were also made to be groups with stronger signal strengths in moving from the first group → the fourth group. PerSD indicates the odds ratio when the sugar-chain signal strength increases by 1 SD (standard deviation).

As understood from tables 14 to 16, for the MPA-binding sugar chains, the ACA-binding sugar chains, the ABA-binding sugar chains, and the Jacalin-binding sugar chains, the greater the signal strength of the quartile group, the greater the indicator indicating a relationship with eGFR rapid decliners. For the SSA-binding sugar chains and the SNA-binding sugar chains, in the quartile group with the highest signal strength, the indicator indicating a relationship with eGFR rapid decliners was greater than in the other groups. As for the GSL_I_B4-binding sugar chains, the greater the signal strength of the quartile group, the smaller the indicator indicating a relationship with eGFR rapid decliners. As for the WA-binding sugar chains and the EEL-binding sugar chains, in the quartile group with the strongest signal strength, the indicator indicating a relationship with eGFR rapid decliners was smaller than the other groups.

The above data suggests that MPA-binding sugar chains, ACA-binding sugar chains, ABA-binding sugar chains, Jacalin-binding sugar chains, SSA-binding sugar chains, SNA-binding sugar chains, WA-binding sugar chains, GSL_I_B4-binding sugar chains, and EEL-binding sugar chains serve as strong renal prognosis factors. In particular, because MPA-binding sugar chains, ACA-binding sugar chains, and ABA-binding sugar chains have a strong relationship to eGFR rapid decliners even in multivariate analysis results, this suggests that they can serve as strong renal prognosis factors independent from eGFR and UACR.

{Result 5: Synergistic Effect on Existing Biomarkers}

Abilities of predicting eGFR rapid decliners by the lectin-binding sugar chains found above were evaluated from a viewpoint of synergistic effect by adding these to a basic model made of only existing biomarkers. Results are indicated in tables 17 and 18.

TABLE 17

| Model | C-index (95% CI) | Difference of c-index (95% CI) | Category-free NRI (95% CI) |
|---|---|---|---|
| Basic model | 0.698 (0.640-0.756) | | |
| +MPA-binding sugar chain | 0.713 (0.657-0.769) | 0.016 (0.000-0.033) | 0.261 (0.040-0.481) |
| +ACA-binding sugar chain | 0.712 (0.655-0.769) | 0.014 (−0.004-0.032) | 0.133 (−0.083-0.350) |
| +ABA-binding sugar chain | 0.712 (0.656-0.768) | 0.015 (−0.004-0.033) | 0.294 (0.032-0.556) |
| +Jacalin-binding sugar chain | 0.703 (0.645-0.760) | 0.005 (−0.003-0.130) | 0.362 (0.024-0.701) |
| +SSA-binding sugar chain | 0.707 (0.649-0.765) | 0.009 (−0.006-0.024) | 0.272 (0.041-0.504) |
| +SNA-binding sugar | 0.704 | 0.006 | 0.261 |

TABLE 17-continued

| Model | C-index (95% CI) | Difference of c-index (95% CI) | Category-free NRI (95% CI) |
|---|---|---|---|
| chain | (0.645-0.763) | (−0.005-0.018) | (0.014-0.507) |
| +VVA-binding sugar chain | 0.704 (0.649-0.760) | 0.007 (−0.010-0.024) | 0.124 (−0.074-0.322) |
| +GSL_I_B4-binding sugar chain | 0.703 (0.645-0.760) | 0.005 (−0.011-0.021) | 0.182 (−0.028-0.393) |
| +EEL-binding sugar chain | 0.699 (0.640-0.757) | 0.001 (−0.013-0.015) | −0.079 (−0.310-0.151) |

TABLE 18

| | | | |
|---|---|---|---|
| +MPA-bindingsugarchain + EEL-bindingsugarchain | 0.722 (0.667-0.778) | 0.024 (0.001-0.048) | 0.422 (0.205-0.639) |
| +SSA-bindingsugarchain + EEL-bindingsugarchain | 0.713 (0.654-0.772) | 0.016 (0.000-0.033) | 0.333 (0.114-0.552) |
| +MPA-bindingsugarchain + WA-bindingsugarchain | 0.725 (0.672-0.779) | 0.028 (0.000-0.057) | 0.198 (−0.039-0.436) |
| +SSA-bindingsugarchain + WA-bindingsugarchain | 0.730 (0.676-0.785) | 0.032 (0.000-0.065) | 0.351 (0.127-0.574) |
| +MPA-bindingsugarchain + GSL_I_B4-bindingsugarchain | 0.722 (0.668-0.777) | 0.025 (0.003-0.047) | 0.363 (0.016-0.610) |
| +SSA-bindingsugarchain + GSL_I_B4-bindingsugarchain | 0.719 (0.663-0.775) | 0.021 (0.000-0.042) | 0.391 (0.177-0.604) |

Variables input to basic model: age, sex, BMI, mean arterial pressure, HbA1c, eGFR, logACR (each being values on the reference date [2012])

As is clear from tables 17 and 18, by adding MPA-binding sugar chains to the basic model, the C-index significantly increased and the NRI was also a significant value. This indicated that MPA-binding sugar chains have a significant synergistic effect on the basic model even independently. Likewise, the NRI was also a significant value when the ABA-binding sugar chains, the Jacalin-binding sugar chains, the SSA-binding sugar chains, and the SNA-binding sugar chains were added to the basic model. This suggested that adding the above lectin-binding sugar chains independently to the basic model significantly increases the prediction ability of eGFR rapid decliners.

Independently, the WA-binding sugar chains, the GSL_I_B4-binding sugar chains, and the EEL-binding sugar chains did not have a significant synergistic effect on the basic model. However, it was shown that adding these to the basic model in combination with MPA-binding sugar chains (having specificity with regard to Galβ1-3GalNAc) or SSA-binding sugar chains (having specificity with regard to Siaα2-6Gal/GalNAc) significantly increases the prediction ability of eGFR rapid decliners (the C index significantly increased, and the NRI value also exhibited a significantly high value). As such, a significant synergistic effect can be anticipated on the basic model even when WA-binding sugar chains, GSL_I_B4-binding sugar chains, or EEL-binding sugar chains and the sugar chains of (i) or (ii) below are combined.

(i) ACA-binding sugar chains, ABA-binding sugar chains, and/or Jacalin-binding sugar chains (each having specificity with regard to Galβ1-3GalNAc)
(ii) SNA-binding sugar chains (having specificity with regard to Siaα2-6Gal/GalNAc).

Synthesizing the above results suggests that the sugar chains of (i) and (ii) below can, even independently, increase a prediction ability of reduced renal function by being combined with existing markers.

(i) MPA-binding sugar chains, ACA-binding sugar chains, ABA-binding sugar chains, and Jacalin-binding sugar chains (each having specificity with regard to Galβ1-3GalNAc)
(ii) SSA-binding sugar chains and SNA-binding sugar chains (each having specificity with regard to Siaα2-6Gal/GalNAc).

Furthermore, this suggests that in addition to (I) the existing biomarkers and (II) the sugar chains having specificity with regard to the above lectins (MPA, ACA, ABA, Jacalin, SSA, and SNA), further combining (III) WA-binding sugar chains, GSL_I_B4-binding sugar chains, or EEL-linked binding chains further increases the prediction ability of renal function.

INDUSTRIAL APPLICABILITY

The present invention can be used, for example, to predict reduced renal function. As such, the present invention can be used in the field of diagnostic devices.

What is claimed is:

1. A method of determining an increased risk for reduced renal function in a subject in need thereof, comprising the steps of:
   a) determining a level of at least one of Galβ1-3GalNAc and Siaα2-6Gal/GalNAc in a sample from said subject; and
   b) comparing the level of said at least one of
      (i) Galβ1-3GalNAc and
      (ii) Siaα2-6Gal/GalNAc to a reference value,
   wherein said level of at least one or both of Galβ1-3GalNAc and Siaα2-6Gal/GalNAc above said reference value indicates an increased risk of reduced renal function in said subject.

2. The method of claim 1, further comprising the step of:
   c) determining a level of at least one type of sugar chain selected from α-GalNAc, Galα, and Galα1-3Gal in said sample from the subject.

3. The method of claim 2, further comprising determining a level of a sugar chain that binds with at least one lectin selected from a group consisting of VVA, GSL_I_B4, and EEL.

4. The method of claim 3, wherein the subject has one or more-types of diseases selected from diabetes, hypertension, dyslipidemia, obesity, and hepatic steatosis.

5. The method of claim 2, wherein the subject has one or more-types of diseases selected from diabetes, hypertension, dyslipidemia, obesity, and hepatic steatosis.

6. The method of claim 1, further comprising determining a level of a sugar chain that binds with at least one lectin selected from a group consisting of MPA, ACA, ABA, Jacalin, SSA, and SNA.

7. The method of claim 6, wherein the subject has one or more-of diabetes, hypertension, dyslipidemia, obesity, and hepatic steatosis.

8. The method of claim 1, wherein the subject is a subject with one or more types of diseases selected from diabetes, hypertension, dyslipidemia, obesity, and hepatic steatosis.

9. The method of claim 1, wherein Gal β 1-3GalNAc and Sia α 2-6Gal/GalNAc levels are determined via a method selected from a lectin assay, liquid chromatography, mass spectrometry, ELISA, two-dimensional electrophoresis, a protein array, a bead assay, flow cytometry, and Bio-Plex® Multiplex Immunoassay System.

10. The method of claim 1, further comprising treating a subject determined to have an increased risk of reduced renal function.

11. The method of claim 10, wherein said subject is treated with one or more of dialysis, insulin, anti-hypertensive, anti-diabetic, anti-hyperlipidemic and anti-hyper-uricemic.

12. A method of determining an increased risk of reduced renal function in a subject in need thereof, comprising the step of:
   a) determining a level of a sugar chain that binds with at least one lectin selected from MPA, ACA, ABA, Jacalin, SSA, SNA, VVA, GSL_I_B4, and EEL in a sample from said subject; and
   b) comparing said at least one level of said sugar chain to a reference value, wherein levels of at least one of MPA, ACA, ABA, Jacalin, SSA, and SNA above said reference value, indicates an increased risk of reduced renal function in said subject and, or,
   c) comparing said at least one level of said sugar chain to a reference value, wherein levels of at least one of VVA, GSL_I_B4, and EEL below said reference value indicate an increased risk of reduced renal function in said subject.

13. The method of claim 12, wherein the subject has one or more-types of diseases selected from diabetes, hypertension, dyslipidemia, obesity, and hepatic steatosis.

14. The method of claim 12, wherein MPA, ACA, ABA, Jacalin, SSA, SNA, VVA, GSL_I_B4, and EEL levels are determined via a method selected from a lectin assay, liquid chromatography, mass spectrometry, ELISA, two-dimensional electrophoresis, a protein array, a bead assay, flow cytometry, and Bio-Plex® Multiplex Immunoassay System.

15. The method of claim 12, further comprising treating a subject determined to have an increased risk of reduced renal function.

16. The method of claim 15, wherein said subject is treated with one or more of dialysis, insulin, anti-hypertensive, anti-diabetic, anti-hyperlipidemic and anti-hyper-uricemic.

* * * * *